United States Patent
Hovorka

(10) Patent No.: US 9,730,585 B2
(45) Date of Patent: *Aug. 15, 2017

(54) ADJUSTABLE PNEUMATIC SUPPORTING SURFACE

(71) Applicant: HLZ Innovation, LLC, Austin, TX (US)

(72) Inventor: George Hovorka, East Boston, MA (US)

(73) Assignee: HLZ Innovation, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/456,364

(22) Filed: Aug. 11, 2014

(65) Prior Publication Data

US 2014/0350434 A1    Nov. 27, 2014

Related U.S. Application Data

(63) Continuation of application No. 12/587,230, filed on Oct. 2, 2009, now Pat. No. 8,801,635.

(60) Provisional application No. 61/195,073, filed on Oct. 3, 2008.

(51) Int. Cl.
| | |
|---|---|
| A61B 5/103 | (2006.01) |
| A61B 5/00 | (2006.01) |
| A61B 5/03 | (2006.01) |
| A61B 5/11 | (2006.01) |
| A61G 7/057 | (2006.01) |

(52) U.S. Cl.
CPC .......... *A61B 5/0053* (2013.01); *A61B 5/0048* (2013.01); *A61B 5/1126* (2013.01); *A61B 5/445* (2013.01); *A61G 7/05776* (2013.01); *A61B 5/6892* (2013.01); *A61B 5/7257* (2013.01); *A61B 5/7264* (2013.01); *A61B 2562/0219* (2013.01); *A61B 2562/168* (2013.01)

(58) Field of Classification Search
USPC .... 5/600, 710, 713, 715, 727; 600/552, 553, 600/587; 702/98
See application file for complete search history.

(56) References Cited

U.S. PATENT DOCUMENTS

| | | |
|---|---|---|
| 802,526 A | 10/1905 | Hanson |
| 945,234 A | 1/1910 | Hinsdale |
| 1,296,359 A | 3/1919 | Brown |
| 1,772,310 A | 8/1930 | Hart |
| 2,415,150 A | 2/1947 | Stein |
| 2,719,986 A | 10/1955 | Rand |

(Continued)

FOREIGN PATENT DOCUMENTS

| | | |
|---|---|---|
| EP | 0168213 A2 | 1/1986 |
| EP | 0489310 A1 | 6/1992 |

OTHER PUBLICATIONS

International Search Report and Written Opinion, PCT/US2009/005434, dated Jun. 3, 2010.

*Primary Examiner* — Sean Dougherty
(74) *Attorney, Agent, or Firm* — Lerner, David, Littenberg, Krumholz & Mentlik, LLP

(57) ABSTRACT

An apparatus and method are adapted for characterizing human tissue type. A plurality of inflatable bladders enable the application of kinetic energy to the human tissue. Collected data responsive to the applied kinetic energy differentiates between different tissue types and patient loading. The data can be routed via a network to a remote location.

12 Claims, 24 Drawing Sheets

(56) References Cited

U.S. PATENT DOCUMENTS

| | | | |
|---|---|---|---|
| 3,789,674 A | 2/1974 | Anderson et al. | |
| 4,197,837 A | 4/1980 | Tringali et al. | |
| 4,542,547 A | 9/1985 | Sato | |
| 4,567,771 A | 2/1986 | Nelson et al. | |
| 4,592,235 A | 6/1986 | Fink | |
| 4,646,754 A * | 3/1987 | Seale | 600/587 |
| 4,771,792 A * | 9/1988 | Seale | 600/587 |
| 4,797,962 A | 1/1989 | Goode | |
| 4,825,486 A | 5/1989 | Kimura et al. | |
| 5,003,654 A | 4/1991 | Vrzalik | |
| 5,006,984 A * | 4/1991 | Steele | 600/587 |
| 5,044,029 A | 9/1991 | Vrzalik | |
| 5,052,067 A | 10/1991 | Thomas et al. | |
| 5,103,519 A | 4/1992 | Hasty | |
| 5,142,719 A | 9/1992 | Vrzalik | |
| 5,152,021 A | 10/1992 | Vrzalik | |
| 5,237,501 A | 8/1993 | Gusakov | |
| 5,267,364 A | 12/1993 | Volk | |
| 5,283,735 A | 2/1994 | Gross et al. | |
| 5,368,044 A | 11/1994 | Cain et al. | |
| 5,487,196 A | 1/1996 | Wilkinson et al. | |
| 5,561,412 A | 10/1996 | Novak et al. | |
| 5,603,133 A | 2/1997 | Vrzalik | |
| 5,666,681 A | 9/1997 | Meyer et al. | |
| 5,687,099 A | 11/1997 | Gross et al. | |
| 5,699,038 A | 12/1997 | Ulrich et al. | |
| 5,802,645 A | 9/1998 | Vrzalik | |
| 5,815,864 A | 10/1998 | Sloop | |
| 5,836,891 A | 11/1998 | Dimarogonas | |
| 5,838,223 A | 11/1998 | Gallant et al. | |
| 5,897,510 A | 4/1999 | Keller et al. | |
| 5,915,864 A | 6/1999 | Austin et al. | |
| 5,930,152 A | 7/1999 | Dumont et al. | |
| 5,963,997 A | 10/1999 | Hagopian | |
| 5,966,763 A | 10/1999 | Thomas et al. | |
| 5,983,429 A | 11/1999 | Stacy et al. | |
| 6,132,385 A * | 10/2000 | Vain | 600/553 |
| 6,151,739 A | 11/2000 | Meyer et al. | |
| 6,279,183 B1 | 8/2001 | Kummer et al. | |
| 6,560,804 B2 | 5/2003 | Wise et al. | |
| 6,589,183 B2 | 7/2003 | Yokozeki | |
| 6,611,833 B1 * | 8/2003 | Johnson | |
| 6,799,342 B1 | 10/2004 | Jarmon | |
| 6,928,681 B1 | 8/2005 | Stacy | |
| 7,107,642 B2 | 9/2006 | Wong et al. | |
| 7,260,860 B2 | 8/2007 | Chambers et al. | |
| 7,287,289 B1 | 10/2007 | Hagopian | |
| 7,315,535 B2 | 1/2008 | Schuman | |
| 7,435,232 B2 | 10/2008 | Liebschner | |
| 7,479,120 B2 | 1/2009 | Gregersen | |
| 7,555,436 B2 | 6/2009 | Brown | |
| 7,615,014 B2 | 11/2009 | Omata et al. | |
| 7,850,625 B2 | 12/2010 | Paltieli et al. | |
| 2002/0087511 A1 * | 7/2002 | Johnson | 707/1 |
| 2003/0220556 A1 * | 11/2003 | Porat et al. | 600/407 |
| 2004/0243022 A1 | 12/2004 | Carney et al. | |
| 2004/0249268 A1 | 12/2004 | Da Silva | |
| 2005/0113691 A1 | 5/2005 | Liebschner | |
| 2005/0119643 A1 | 6/2005 | Sobol et al. | |
| 2005/0124920 A1 | 6/2005 | Gregersen | |
| 2005/0234289 A1 | 10/2005 | Anstadt et al. | |
| 2006/0064038 A1 | 3/2006 | Omata et al. | |
| 2006/0162074 A1 | 7/2006 | Bader | |
| 2006/0179579 A1 | 8/2006 | Phillips et al. | |
| 2007/0032727 A1 | 2/2007 | Omata | |
| 2007/0032739 A1 | 2/2007 | Hashimshony et al. | |
| 2007/0032747 A1 * | 2/2007 | Hashimshony et al. | 600/587 |
| 2007/0118027 A1 | 5/2007 | Baker et al. | |
| 2007/0174964 A1 | 8/2007 | Lemire et al. | |
| 2008/0042067 A1 * | 2/2008 | Rousso et al. | 250/363.04 |
| 2008/0052837 A1 | 3/2008 | Blumberg | |
| 2008/0187095 A1 * | 8/2008 | Boone et al. | 378/37 |
| 2008/0200843 A1 * | 8/2008 | Williams et al. | 600/587 |
| 2008/0287750 A1 * | 11/2008 | Hashimshony et al. | 600/301 |
| 2008/0319285 A1 | 12/2008 | Hancock | |
| 2009/0061473 A1 * | 3/2009 | Saxena et al. | 435/29 |
| 2009/0076488 A1 | 3/2009 | Welches et al. | |
| 2009/0287109 A1 | 11/2009 | Ferren et al. | |
| 2010/0087756 A1 | 4/2010 | Egorov et al. | |
| 2013/0274712 A1 | 10/2013 | Schecter | |

* cited by examiner

ANALOG DEVICES ADX L 204 ACCELEROMETER

SKIN OVER SACRUM

ADIPOSE DEPOSIT

INCREASING FREQUENCY ON FFT CHART →

INCREASING FREQUENCY ON FFT CHART

ADJUSTABLE PNEUMATIC SUPPORTING SURFACE

CROSS REFERENCE TO RELATED APPLICATIONS

The present application is a continuation, of U.S. patent application Ser. No. 12/587,230, filed Oct. 2, 2009, which claims the benefit of the filing date of U.S. Provisional Patent Application No. 61/195,073, filed Oct. 3, 2008, the disclosures of which are hereby incorporated herein by reference.

BACKGROUND OF THE INVENTION

The present invention relates in general to an adjustable pneumatic supporting surface, and more particularly, to adjustable pneumatic supporting surfaces responsive to variable loads and different human tissue types.

Alternating pressure mattresses have been in existence for at least 75 years. Segmented air mattresses first came into existence around 1910. U.S. Pat. No. 945,234 describes a pneumatic mattress that in many respects is similar to the low air loss surfaces sold today. Other examples are disclosed in U.S. Pat. Nos. 802,526, and 1,296,359. In 1930, J. D. Hart invented the first pump-driven alternating pressure air mattress. With the exception of the more recent low air loss feature, it is in many respects identical to what is commercially known today. This art is described in U.S. Pat. No. 1,772,310. This patent addresses the problems of bedsores and the concept of shifting the pressure from different portions or areas of the skin with an automated apparatus driving air bladders. U.S. Pat. No. 2,415,150 discloses a pneumatic mattress with small individual cells. An alternating pressure mattress commonly known as a "ripple mattress" is disclosed in U.S. Pat. No. 2,719,986. This particular design of mattress was widely copied and improved upon. Examples of these improvements are disclosed in U.S. Pat. No. 4,197,837. The valve controller system for the mattress was further improved upon as disclosed in U.S. Pat. No. 4,825,486.

Air bladders became known to rotate the entire body as disclosed in U.S. Pat. Nos. 5,003,654, 5,142,719, 5,152,021, 5,603,133, and 5,802,645. Another example is disclosed in U.S. Pat. No. 5,103,519. Rather than rotating the patient in order to reduce bedsores, U.S. Pat. No. 5,267,364 discloses a mattress configured to provide therapeutic waves. In these patents and others to follow, the focus shifted toward reducing the labor required to properly care for a bed-ridden patient. In this case, the patient is being physically rotated by a machine rather than a person.

In another effort to reduce the labor of patient management, there is disclosed in European Application No. EP0168213A2, a servo controlled alternating pressure mattress. The advantage of this mattress is that the equipment operator is no longer involved in adjusting the mattress pressure controls, as this is done automatically through a pressure transducer, which is interfaced to a microprocessor. By measuring the static pressure in the pressure relief surface it is possible to automatically ensure that the air bladders are properly filled at all times. The type of servo utilized in this controller, and in currently employed technology, is a simple limit servo, also known as a bang-bang servo. These systems make their decision on the correct operation of the surface through amplitude measurements of the surface's internal pressure. This approach is disclosed in U.S. Pat. Nos. 5,487,196, 5,044,029, and 6,928,681. The concept of servo control was further expanded by the use of pre-set pressure profiles and a feedback control system. This concept is described in U.S. Pat. No. 4,797,962; see also U.S. Pat. Nos. 5,963,997, 7,287,289, and 5,983,429. Specialized feedback controlled mattresses such as those which treat heel pressure management are disclosed in U.S. Pat. Nos. 5,666,681 and 6,151,739.

The use of limit type servo mechanisms to provide uniform pressure in hospital mattresses and transportation seating is known. An example of a servo controlled transportation seat is disclosed in U.S. Pat. No. 5,930,152. Another example is disclosed in U.S. Pat. No. 4,542,547 which describes a photo-electric control system. A completely mechanical mattress, which provides floatation through servo control, is disclosed in U.S. Pat. No. 5,237,501. Yet other examples which use photo-control are disclosed in U.S. Pat. No. 6,560,804 and U.S. Patent Application No. 2006/0179579A1. Examples of mattresses which utilize electronic control in a pneumatic system are disclosed in European Application No. EPO489,310A1, and U.S. Pat. Nos. 5,687,099, 5,815,864, and 7,107,642. The mattresses use a static pressure measurement which may be a voltage that corresponds to patient pressure as disclosed in the '642 patent, the position of a potentiometer or LVDT as disclosed in the '501 patent, a resistive plastic pressure sensing sensor or a conventional pressure transducer which is utilized in the '310A1 and '099 patents, or a photo-electric limit switch as disclosed in the '547, '804 and '579A1 patents. The use of rate of change rather than a static measurement is disclosed in U.S. Pat. No. 5,915,864 to provide mattress pressure stability.

While these prior art alternating pressure low air loss mattresses reduce the amount of labor required to care for a patient, these mattresses fall short of modern day requirements. For example, they require the use of fixed menus in order to provide the best therapy protocol for the patient. Further, the prior art does not anticipate the legal environment in which hospitals operate today, where there is a need to regularly record and store surface pressure-map information to establish that the patient was receiving optimum surface therapy at all times. The current prior art not only does not anticipate these needs but furthermore, it is not capable of collecting this information because the wrong type of measurements are being used to provide the feedback information for the servo controlled mattress systems.

Since clinical assessment is currently done based on the appearance of the skin, identification of the tissue bearing the load will have significant implications for prevention of the development of pressure ulcers. This automatic characterization of tissue type is enabled by utilizing the present invention. Thus it is possible not only to characterize the weight of the tissue that is above a particular location on the air bladder array but also the type of tissue. With these two pieces of information the microprocessor in the mattress control system will be able to completely characterize the type of patient who is on the surface and where they are located on the surface, for example, the patient's buttocks (adipose tissue) and feet (bony tissue) which possess distinctive frequency spectra.

The escalation of medical costs as led to attempts in the past to streamline the treatment for the prevention of bedsores. Attempts to implement uniform treatment measurement scales, such as the Braden Scale, have heretofore been thwarted by inexact methods of gathering statistical information relevant to the patient's bedsore condition. Certain, rudimentary systems for tracking bedsore information, such as the aforementioned Braden Scale, has been developed.

However, to date, there have been no systems for continuously tracking bedsore development and status, incorporating this information along with patient mobility on the treatment surface in an automated fashion according to the recorded bedsore status and patient mobility data.

Accordingly, there is an unsolved need for an adjustable pneumatic support surface such as a mattress and the like which is able to diagnose the patient and create a custom designed therapy protocol with the objective of the supporting surface being able to take preventative action before a breakdown of patient tissue occurs. There is a further need for an integrated system capable of tracking and analyzing tissue abnormality development and patient mobility on a pressure relief surface.

SUMMARY OF THE INVENTION

It is an object of this invention to provide tissue abnormality prevention surfaces, which are automatically adaptable to the particular patient.

It is yet another object of this invention to provide bedsore prevention surfaces, which are automatically adaptable to the particular patient, and to where the patient is located on the surface.

It is another object of this invention to provide a pressure mapping system that is able to differentiate between the different types of tissues that can be mapped on a segment by segment basis.

It is another object of the invention to provide a tissue abnormality reducing surface, which is capable of combining pressure-mapping information with tissue characterization information such that it can be utilized internally to provide the ideal patient therapy protocol. This data can also be exported to a host computer over a network.

It is another object of the invention to provide information as to where the patient is located on the pressure relief surface in order to optimize the therapy.

It is another object of this invention to provide a tissue abnormality reducing surface, which utilizes the least amount of energy by only powering those air bladders, which are in patient pressure contact.

The present invention describes a method of operation of a pressure relief surface, which utilizes a novel sensor and analysis means. Previously, amplitude measurements of the pressure signals were utilized for feedback control, which due to the measurement method, has limitations. This can be understood by evaluating the two waveforms shown in FIG. 1 which were collected from an accelerometer sensor attached to one of the percussion bladders on a Stryker Model 2950 bed surface. In FIG. 1, the top waveform is the amplitude of a sensor attached to the percussion bladder over time while the bottom waveform is the same signal in frequency space.

In the field of electronics frequency space, also known as frequency domain, is a term of art used to describe the analysis of signals with respect to frequency rather than time. For example, a time-domain graph, shown as the top wave form in FIG. 1, indicates how a signal changes over time, whereas a frequency space graph, shown as the bottom wave form in FIG. 1, indicates how much of the signal lies within each given frequency band over a range of frequencies. A given signal can be converted between time and frequency domains with a pair of mathematical operators called a transform. An example is the Fourier transform whereas the inverse Fourier transform converts the frequency domain function back to a time function.

As shown in FIG. 1, the amplitude signal collected from the sensor mounted on the percussion bladder appears to be a nearly perfect sinusoid. But when this waveform is analyzed in frequency-space, several distinct resonators can be seen. This phenomenon can be understood by comparing frequency space analysis of a sine wave to a square wave, which is shown in FIG. 2.

As can be seen in FIG. 2, the pure sine wave has a single peak in frequency space while the square wave is composed of an infinite number of Bessel functions which are shown as a decreasing series of spectral peaks in frequency space.

In accordance with one embodiment of the invention, when work is performed on tissue by applying kinetic energy to it, this energy will be dissipated over time as heat in the tissue. The rate at which this energy is dissipated by the tissue is commensurate to the type of tissue. For example, adipose tissue is able to easily absorb kinetic energy due to its high damping coefficient. On the other hand, skin over bone tissue is only able to poorly absorb kinetic energy due to its low damping coefficient, and thus, this energy will be present in the tissue for a longer time in the form of mechanical energy before it is converted into heat.

This difference in the mechanical conversion into heat by a particular tissue type can be determined through measurements made in frequency space or rate based analysis. This invention contemplates applying the mechanical energy in different formats such as a continuous oscillating function or as an impulse or through the inflation of an air bladder from one level of inflation to another.

Further, the invention contemplates detecting the dissipation of the mechanical energy via a variety of detecting means, for example, wide band sensors such as accelerometers, pressure sensors and strain gauges. Common to all methods contemplated in the invention is the measurement of the dissipation of the mechanical energy, no matter how applied, by the tissue through a variety of these sensors combined with, for example, frequency space analysis and rate based analysis.

The waveforms from sensors located on the pneumatic bed surface are someplace between those of a pure sine wave and the harmonic rich content of a square wave. The exact nature of the signal content depends on the patient tissue type into which the bladder is being accelerated. The present invention incorporates these differences in the waveforms between the bladder being accelerated into bony tissue, into adipose tissue, and into an unloaded surface.

These differences in the frequency spectra can be used to provide control for the bed surface because they can provide information about the type and status of the tissue that is located over a particular sensor. When this data is measured over time, small changes in tissue condition can be detected, which are indicative of a pending skin breakdown. Thus, the control computer can make decisions in real time on how to best optimize the bed surface for the patient.

The present invention enables features which include: (1) Tissue determination on a segment by segment basis. This will enable optimized treatment for each section of the patient. For example a different therapy protocol for the adipose tissue vs. more fragile bony tissue; (2) The ability to measure the patient's mobility on the surface; (3) The ability to track the patient as they reposition themselves on the surface and provide optimized therapy wherever they are on the surface. This will include the ability to measure the position of the patient lying vs. sitting and to provide the optimal therapy protocol at all times; and (4) The ability to create diagnostic metrics on the patient's pressure relief status which can be utilized by both the professional staff and the institution's senior management to track the pressure relief situation.

The present invention utilizes multiple sensors in multiple locations on the bed surface in order to provide wide bandwidth information, which is utilized to control the surface. In accordance with one embodiment of the invention, providing a high density of sensors provides higher quality information. Furthermore, this information gathered from these multiple sensors is utilized to create diagnostic data concerning the patient's condition, which is medically useful. In addition, the diagnostic data can be combined with conventional thermography.

The present invention provides a bed surface having an improved support surface assembly, and provides a bed suitable for providing a variety of therapies to the patient through an improved feedback control system. The support surface in accordance with one embodiment of the present invention preferably includes an array of independently inflatable bladders. In one preferred embodiment of the support surface, a matrix of sensors in an array is capable of making rate-based or frequency space measurements, which can provide detailed tissue characterization information concerning the patient resting on the surface The output of the sensors can be connected via either an analog multiplexing system or a CAN digital data link to a conventional microprocessor system, which regulates a plurality of proportional valves that modulate the airflow between a compressor or blower assembly and the air bladders, strap system or other means of elevating selected areas of the patient.

It is contemplated that the data from these sensors can be used in conjunction with other sensor information such as thermography, and pattern recognition software, to provide a map that shows where this information is being measured on the patient's body. One method to achieve this objective would be to combine data from rate based measurement sensors with data from conventional pressure mapping sensors. This rate based measurement and mapping data will provide an outline of the patient, and it will also show the various pressure points on the patient's body. This mapping information can then be combined with the skin characterization data determined by the rate based sensors to enable improved diagnostic data.

The present invention describes an apparatus for characterizing tissue type of a patient, comprising a surface adapted for supporting an anatomical portion of a patient; at least one sensor coupled to the surface, the sensor operable to collect data reflective of a load exerted on the surface by the anatomical portion; and a processor operable to analyze the collected data and to characterize a tissue type of the anatomical portion. The invention further including a network over which data can be transmitted by the processor.

The present invention further describes a method for characterizing tissue type of a patient, comprising the steps of providing a surface adapted for supporting an anatomical portion of a patient; collecting data reflective of a load exerted on the surface by the anatomical portion with at least one sensor disposed on the surface; and analyzing the collected data and characterizing a tissue type of the anatomical portion.

The present further describes an apparatus for characterizing human tissue type comprising a surface adapted for applying kinetic energy to an anatomical portion of a human supported thereon; and at least one sensor associated with the surface responsive to the rate of dissipation of the applied kinetic energy, whereby the rate of dissipation of the applied kinetic energy is indicative of the tissue type of the anatomical portion The present invention further describes an apparatus for supporting a human having different tissue types comprising: a plurality of inflatable bladders having a surface adapted for applying kinetic energy to an anatomical portion of a human supported thereon; and at least one sensor associated with the surface responsive to the rate of dissipation of the applied kinetic energy, whereby the rate of dissipation of the applied kinetic energy is indicative of the tissue type of the anatomical portion.

The present invention further describes a method for characterizing tissue type of a human, comprising providing a plurality of inflatable bladders having a surface adapted for applying kinetic energy to an anatomical portion of a human supported thereon; applying the kinetic energy to the anatomical portion; collecting data reflective of the rate of dissipation of the applied kinetic energy; and analyzing the collected data to characterize the tissue type of the anatomical portion.

The present invention further describes an apparatus for characterizing the tissue type of a human, comprising a surface adapted for supporting an anatomical portion of a human; at least one sensor coupled to the surface, the sensor operable to collect data reflective of a load exerted on the anatomical portion by the surface; and data analysis means for analyzing the collected data to characterize the tissue type of the anatomical portion.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof may best be understood by reference to the following detailed description when read with the accompanying drawings in which:

DETAILED DESCRIPTION

Figure 1:
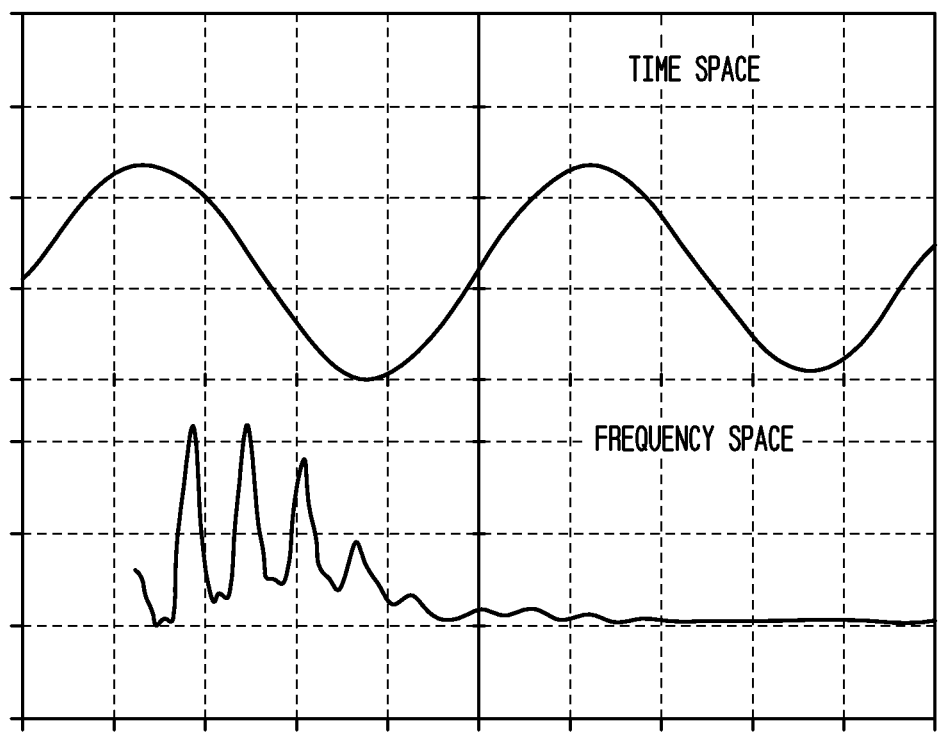
FIG. 1 is a frequency graph in which top waveform is the amplitude of a sensor attached to a percussion bladder while the bottom waveform is the same signal in frequency space.
Figure 2:
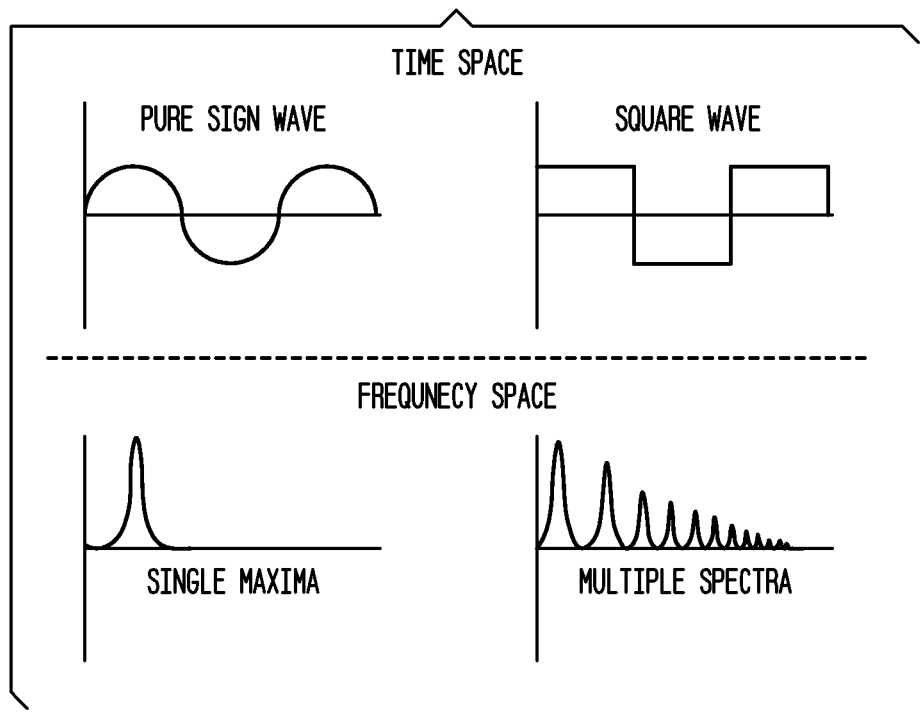
FIG. 2 is a frequency space comparison of a sine wave and square wave.

In describing the preferred embodiments of the invention illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose.

The various embodiments of the present invention are described in the examples below. Examples 1 and 2 generally apply kinetic energy to the tissue through inflation of an air bladder and an inflation rate measurement performed to generally differentiate the type and location of tissue over an entire bladder, while the other Examples 3 through 7 also utilize the principle of applying kinetic energy to a particular area of tissue and then measuring how the tissue in this particular area dissipates this energy into heat through frequency space analysis means. In accordance with the present invention, there are multiple ways of obtaining the particulars of the kinetic energy dissipation for the different tissue types in the particular area of the bed surface.

Two inflation rate based measurement methods in accordance with the present invention will now be described. One method is a differential pressure rate measurement method in which the inflation rate-data from two pressure sensors, one placed at each end of a bladder is utilized to characterize the patient tissue in the particular area of the bed surface, as further described in Example 1. The second method utilizes an accelerometer with measurement performed by measuring the rate of acceleration of the sensor in the earth's uniform gravitational field as described in Example 2.

Figure 3:
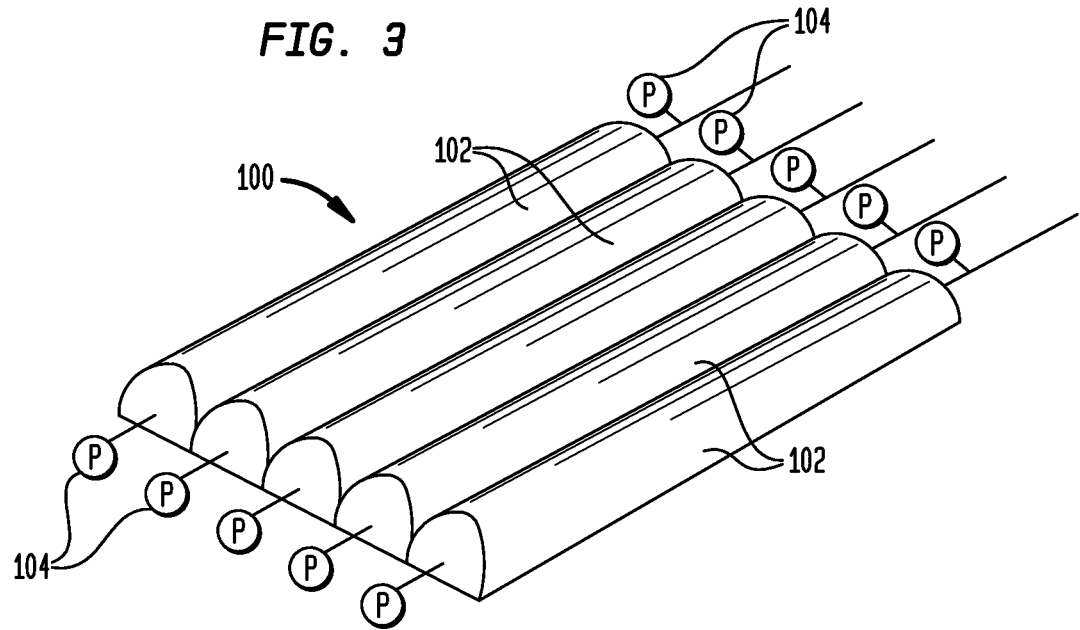
FIG. 3 shows differential pressure measurements on a bladder surface.
Figure 4:
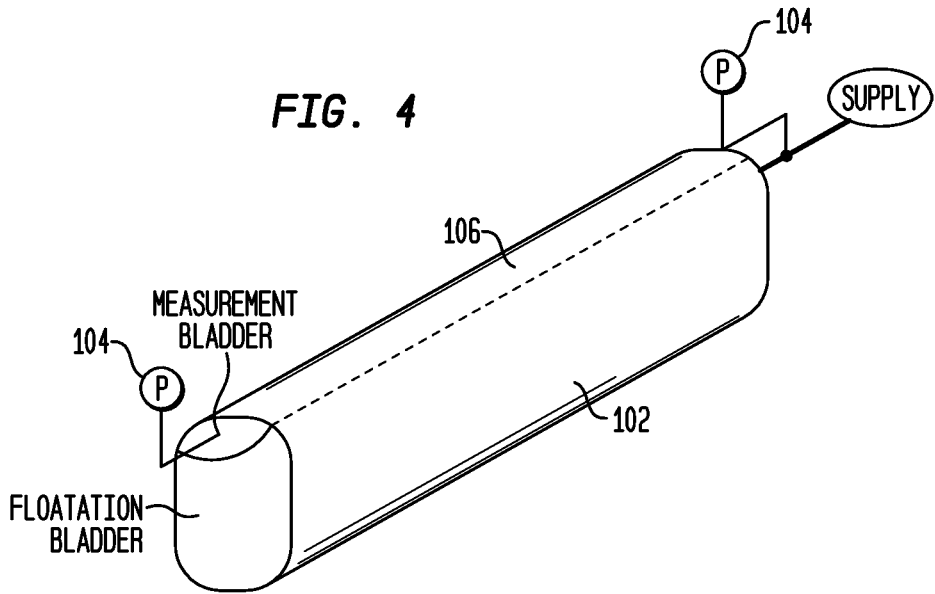
FIG. 4 shows measurement and floatation bladders in a single housing.

A diagram of the differential pressure measurement method on a bladder array 100 composed of a plurality of inflatable bladders 102 is shown in FIG. 3. In accordance with one embodiment of the invention, a pressure sensor 104 is connected to each end of the bladders 102. The pressure sensors 104 measure the pressure across the entire bladder volume. It should be understood that it is not essential that the differential pressure across the entire bladder be measured, but rather, in accordance with another embodiment, a measurement bladder 106 with significantly smaller cross-section may be placed on top of a larger cross-section floatation bladder 104 in order to maximize the signal differentiation from different types of tissue, as shown in FIG. 4. As a result, the measurement bladder has a smaller volume than that of the floatation bladder. The main function of the floatation bladder 104 is to support the patient. The bladders 102, 106 may be integrally formed as one piece, or separately formed and adhered to each other.

EXAMPLES

The following examples are presented to illustrate the invention, which is not intended to be in any way limited thereto, since numerous modifications and variations therein will be apparent to one skilled in the art.

Example 1—Rate Based Measurement Utilizing Differential Pressure Sensors

Figure 5:
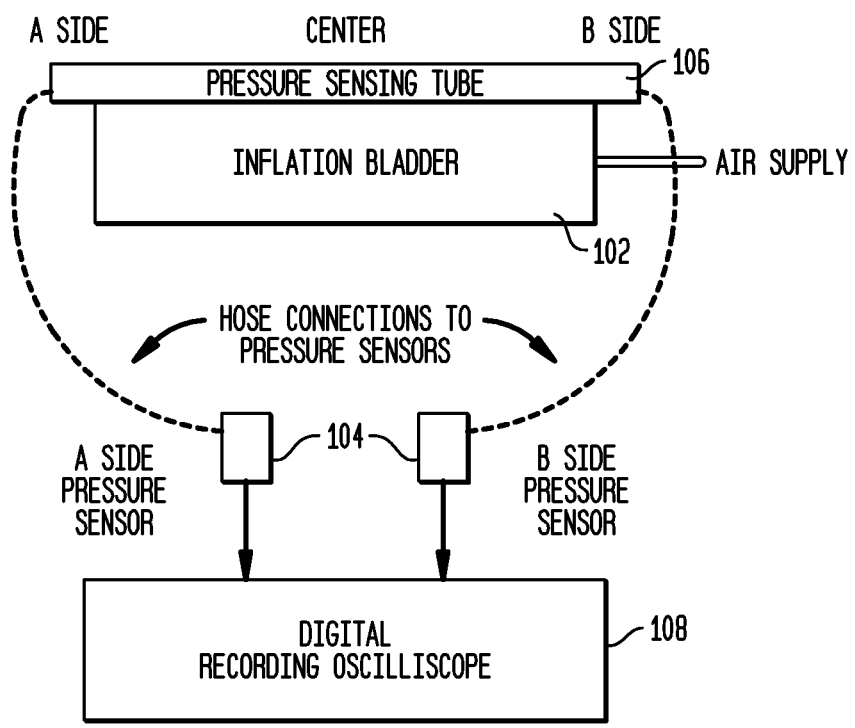
FIG. 5 is a schematic diagram of differential pressure measurement, rate based apparatus.

Referring to FIG. 5, the floatation bladder 102, over which the measurement bladder 106 has been placed, is arranged such that the measurement bladder is in between the floatation bladder and the patient. On either end of the measurement bladder 106, pressure sensors 104, identical to that disclosed in Example 4, are attached. The analog output of these sensors is connected to, for example, a Tektronix Model 3034 Digital recording oscilloscope 108.

Figure 6:
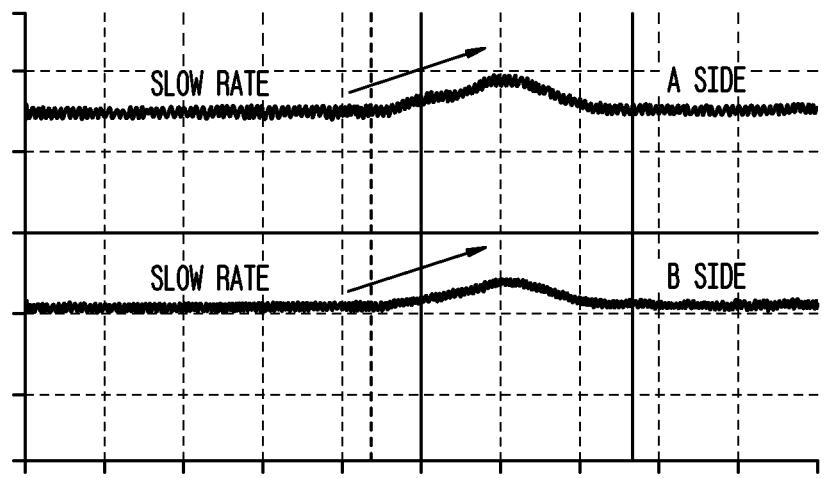
FIG. 6 shows data from adipose tissue phantom placed in the center of the sensing tube.
Figure 7:
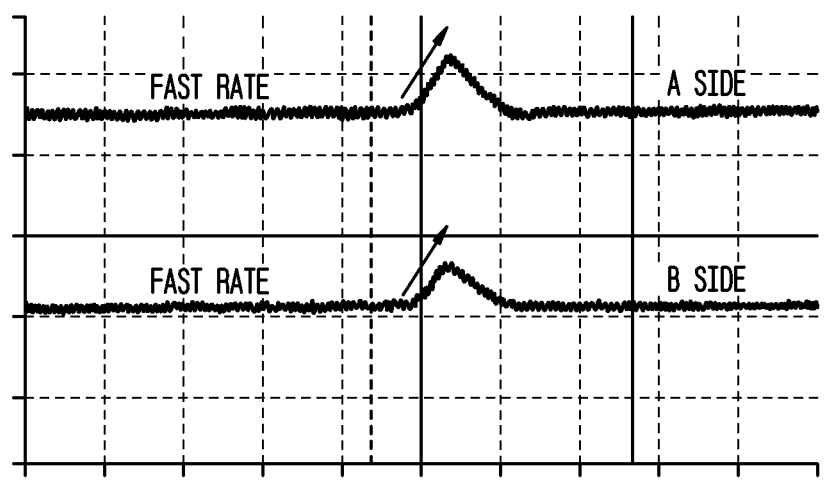
FIG. 7 shows data from skin over sacrum tissue phantom placed in the center of the sensing tube.

The floatation bladder 102 is inflated in a conventional way and tissue phantoms which represent different tissue types (which are further described in Example 5) are place on the floatation bladder in differing locations. The differentiation of different types of tissue is shown in FIGS. 6 and 7. In FIG. 6 there is shown data from an adipose tissue phantom placed in the center of the measurement bladder. In FIG. 7 there is shown data from a skin over sacrum tissue phantom placed in the center of the measurement bladder. FIGS. 6 and 7 evidence that the rate of pressure amplitude increase is significantly slower with the adipose tissue phantom compared to the skin over sacrum phantom.

Figure 8:
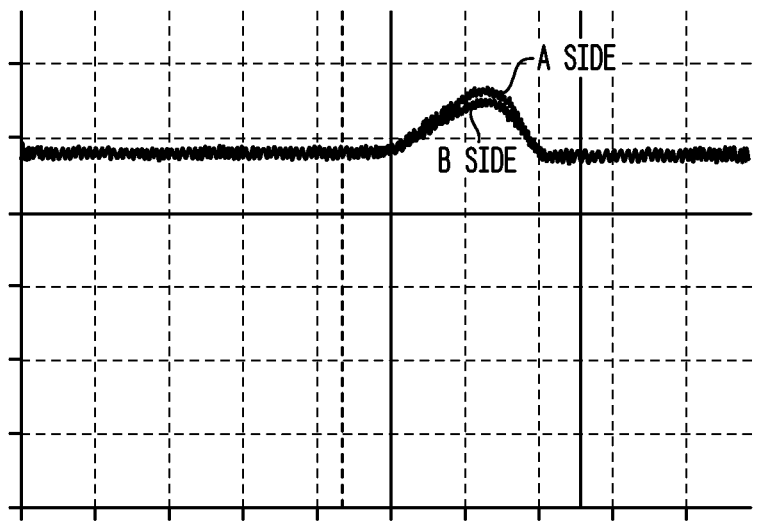
FIG. 8 shows a signal detected from scan over sacrum phantom with the A side and B side signals laid over each other.

These Figures evidence that the more flaccid tissue is able to perform work on the air column inside the measurement bladder at a slower rate compared to the hard skin over sacrum phantom. Therefore, it is possible to differentiate between hard and soft tissue types do to the differences in inflation rate data. This rate data reflects the ability of the tissue to dissipate kinetic energy imparted by the measurement bladder. Shown in FIG. 8 is the signal detected from scan over sacrum phantom with the A side and B side signals laid over each other. It can be seen that the two waveforms from the two pressure sensors 104 are nearly identical when laid over each other.

Figure 9:
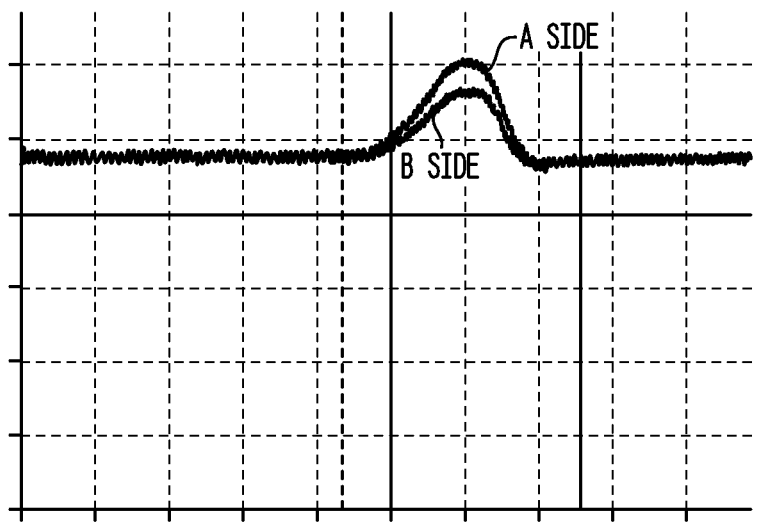
FIG. 9 shows data from skin over sacrum place close to the A side of the pressure sensing tube.

The location of the tissue type determined can be identified on the floatation bladder. In this regard, the skin over sacrum phantom is placed at either end of the measurement bladder and data gathered as shown in FIG. 9, which is the skin over sacrum phantom placed close to the A sensor side of the measurement bladder. The data created with the pressure sensor located near the B side of the measurement bladder is shown in FIG. 10.

Figure 10:
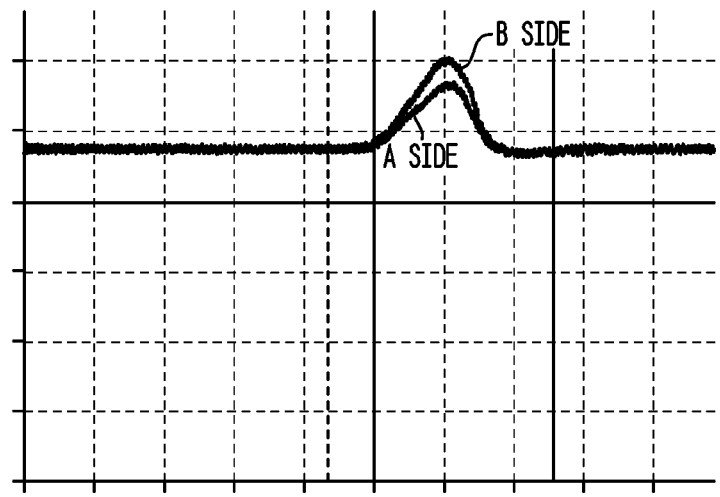
FIG. 10 shows data from skin over sacrum place close to the B side of the pressure sensing tube.

From FIGS. 9 and 10, the signal from the skin over sacrum phantom has larger relative amplitude depending on the phantoms proximity to the nearest pressure sensor. Therefore, one can differentiate between different types of tissue utilizing the invention, in addition to determining where the patient is located on a particular bladder. These two pieces of information when combined will provide a composite picture of where the patient is located on a particular surface and the types of tissue along with their geographical arrangement of the tissues on that surface. The ability to know where the patient is located on the surface and the patient's movement over time may be of diagnostic use, for example, for measuring patient movement patterns.

Example 2—Rate Based Measurement Utilizing an Accelerometer

Figure 11:
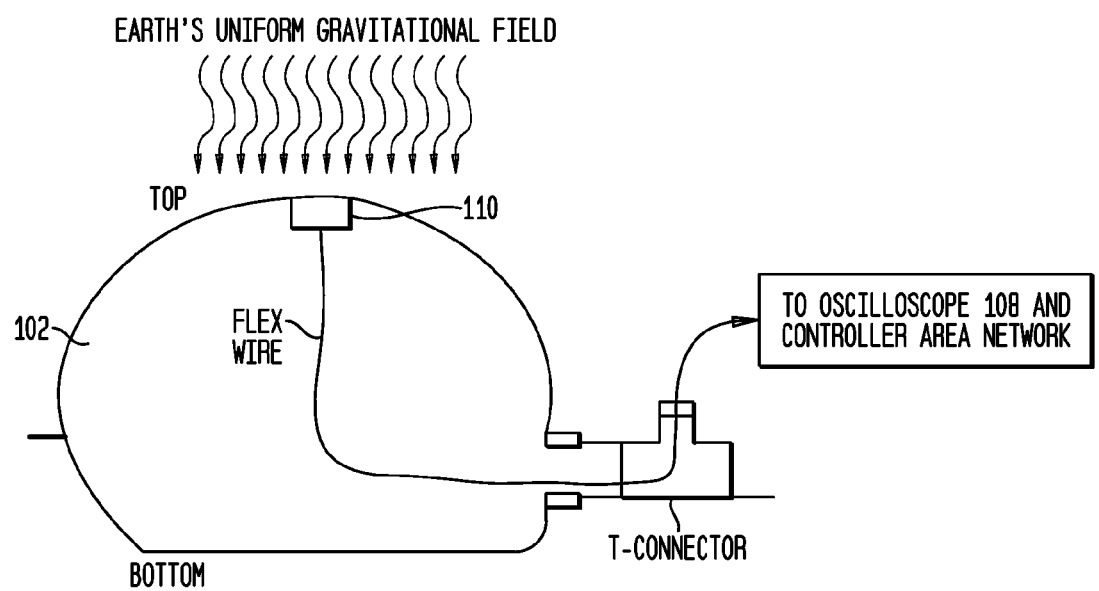
FIG. 11 shows implementation of an Analog Devices ADX L 204 accelerometer to provide rate-data on a pneumatic surface.

Alternatively to using a pressure sensor at each measurement end of the floatation or measurement bladder, another embodiment of the invention is to utilize a micro-accelerometer sensor 110, for example such as one manufactured by Analog Devices (ADX L 204). As shown in FIG. 11, the accelerometer 110 is placed at one end of the floatation bladder 102, internally or externally on the bladder, and utilizes the Earth's uniform gravitational field as the reference. Other, accelerometers can also be used such as those described in U.S. Pat. Nos. 4,592,235, 3,789,674 and 4,567,771 which utilize spring mass sensors, the disclosures of which are incorporated herein by reference. In addition, other types of accelerometers such piezoelectric are also suitable for this application. The signals from the accelerometer are sent to an Oscilloscope 108 which may be connected to an area network.

Figure 12:
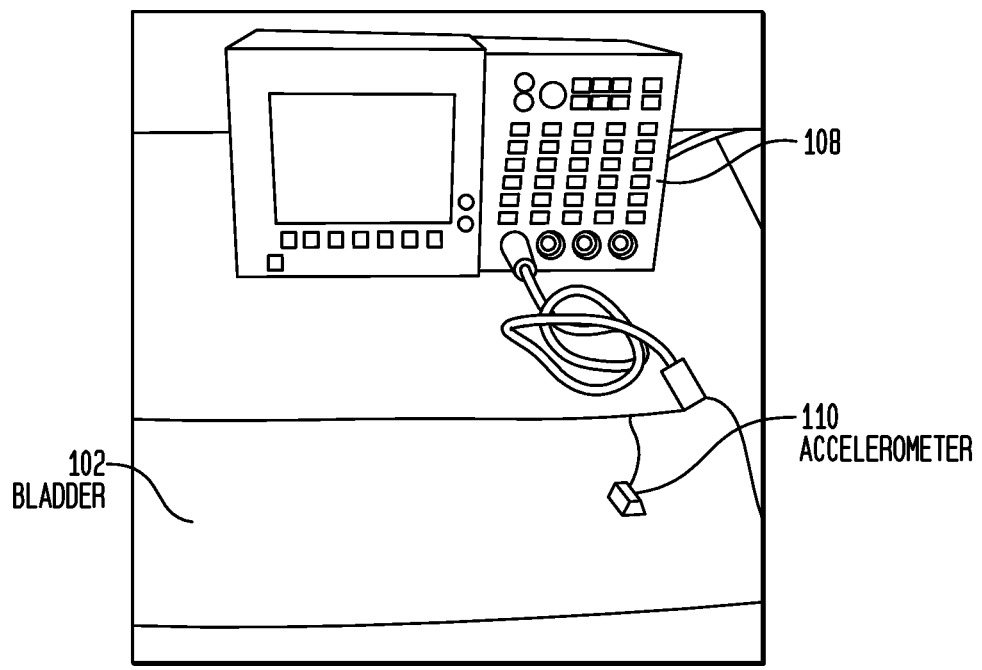
FIG. 12 shows an accelerometer attached to a test bladder.
Figure 13:
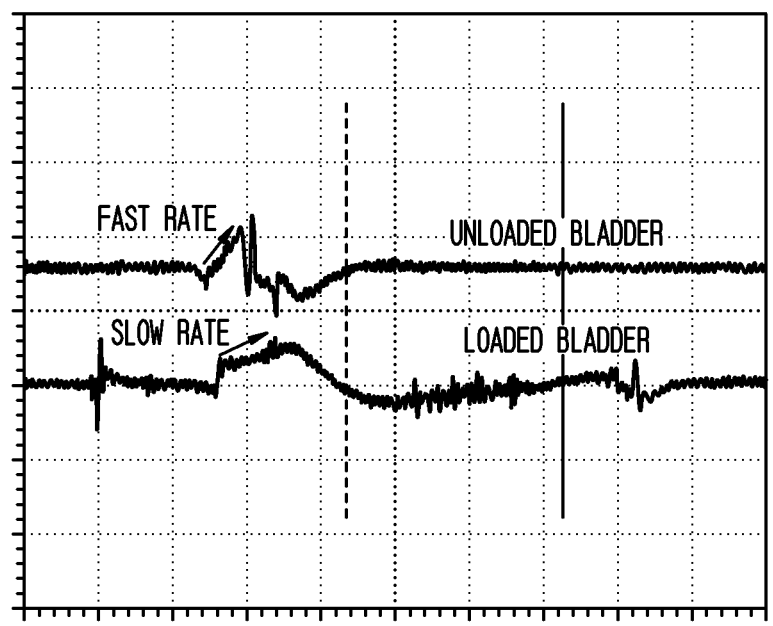
FIG. 13 shows data from Analog Devices ADX L 204 positioned on top of a pressure relief bladder.

As further shown in FIG. 12, the floatation bladder 102 is inflated and the rate of inflation is measured with an accelerometer 110 positioned externally on its surface. The oscilloscope 108 is used to gather the data. The pressure air source is connected to the left side of the floatation bladder 102 and the accelerometer 110 mounted externally to the right end of the bladder. The inflation rate measurements are performed with the bladder unloaded and loaded with weight. The data from the apparatus is shown in FIG. 13 evidencing that the loaded and unloaded bladders have different acceleration rate characteristics. In this example, the kinetic energy, which is dissipated by the load, is supplied through the inflation of the bladder. The differences in rate between the loaded and unloaded bladder demonstrate that this analysis means is able to detect this energy dissipation through rate measurements.

Frequency Space Analysis

In accordance with the present invention, there are multiple ways of obtaining the particulars of the kinetic energy dissipation for the different tissue types. Five frequency space based measurement methods in accordance with the present invention will now be described.

Example 3

Figure 14:
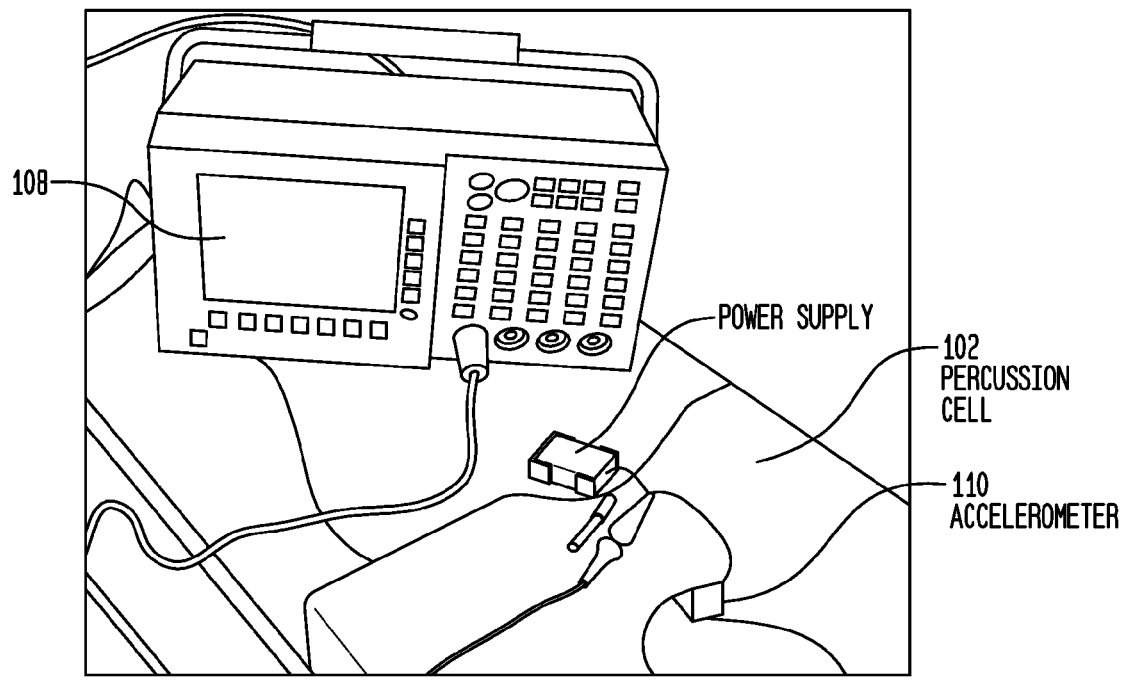
FIG. 14 shows a test configuration for tissue characterization experiments.

Using Fast Fourier Transform (FFT) analysis, kinetic energy is supplied by a small inflation bladder 112 in continuous inflation/deflation oscillation and an accelerometer 110 used to measure the absorption of this energy by the tissue placed over the accelerometer, see FIG. 14.

Through the use of frequency-space analysis it is possible to characterize the type of tissue which is being elevated by the surface of the inflation bladder. Although the data taken is the repetitive motion of the inflation bladder, it should be understood that FFT analysis is intended to predict the probability of frequencies in a continuous function such as a square wave oscillator. For burst functions, such as that provided by the accelerometer sensors in Examples 5-7, the software inside the oscilloscope stores the burst of data into memory and then "plays" it through the FFT algorithm many times until a spectra is derived. It should also be understood that other transforms besides FFT may be used for this analysis. Such as the Laplace transform; wavelet transform; Hankel transform; Mellin transform; Hadamard transform; Karhunen-Loeve transform or Hilbert transform may be used to a produce frequency-domain output from time-domain input. The preferred method of transformation is the use of the wavelet transform.

The Mellin transform can also be combined into a Fourier-Mellin transform which will reduce or eliminate the need to attempt corrections due to rotation or scaling (i.e., proportional shrinking or stretching of a sensor surface under the patient). Thus, the Fourier-Mellin transform could be of particular use to eliminate the variability of different patients having different weights when searching for tissue characteristics. In addition, it could be used to compensate for changes in the sensor surface due to the shifting of patient weight.

Digital filters could be employed to improve the signal to noise ratio of the detection method. For example, in digital image extraction, the utilization of preprocessing techniques such as the use of a Sobel filter or median filter prior to feature extraction are well known. These preprocessing techniques are, however, based on the relative magnitudes of adjacent pixels, or in this case sensors, rather than on the variations of energy received from the sensor. Other examples include the Radon transform and Gabor filters.

After the feature vector representing a particular area of tissue is extracted from the data matrix of the surface, techniques for image processing provide a number of approaches for determining that the sensor data corresponds to the tissue in regard to one of several predetermined classes of tissue. This determination can be made statistically by the use of stored decision rules corresponding to individual classes of tissue. These rules are obtained by training the tissue classification system with pre-determined characteristics for each type tissue (bony, adipose and types in between these characteristics). This can be done with a Bayes classifier which is used to compare the tissue features from an unknown sensor signal with the derived decision rules.

The decision rules software can be carried out by a digital signal processing (DSP) microcontroller such as a Microchip type dsPIC30F2010 which employs a 10-bit, analog-to-digital Converter (A/D) to convert the analog signal from a sensor into a digital form and a 17-bit×17-bit single cycle hardware fractional/integer multiplier along with other attributes of this part to carry out the decision rules calculations. These calculations will then sort the waveforms into their tissue classification. This data will then be sent via the microcontroller's communications port which supports multi-master/slave mode and 10-bit addressing through the data link from the pressure relief surface to the host computer. The 10-bit addressing capabilities of this communications port will enable hundreds or even thousands of sensor/DSP microcontroller pairs on a pressure relief surface to port their data via the data link to the host computer. This computer, with it's software, will be able to format this tissue characterization data, and any changes occurring to this data over time, into a graphical representation such as a 3-dimensional patient avatar at a remote nurse master station and for download into patient records.

As a result, it will be possible to track tissue on a particular location on a patient's body as it transitions from one type of tissue to another (i.e. becomes stiffer over time). This is useful in determining if a particular patient is in danger of developing lesions before they are physically manifested.

The various methods of data transformation are known from "2-D Invariant Object Recognition Using Distributed Associative Memory," H. Webster, G. L. Zimmerman, IEEE Transactions on Pattern Analysis & Machine Intelligence vol. 10, No. 6, pp. 811-821 (November 1988); D. Mendlovic et al., "Shift and Scale Invariant Pattern Recognition using Mellin Radial Harmonics", Opt. Commun. 67(3), July 1988, pp. 172-176; A. Alliney, et al., "On The Registration Of An Object Translating On A Static Background", Pattern Recognition, vol. 29, No. 1, pp. 131-141, 1996; L. G. Brown, "A Survey of Image Registration Techniques", ACM Computing Surveys, vol. 24, No. 4, pp. 325-376, December 1992; F. J. Harris, et al., "On the Use of Windows for Harmonic Analysis with the Discrete Fourier Transform", Proceedings of the IEEE, vol. 66, No. 1, pp. 51-82, January 1978; Gabor, et al., "Theory of Communication," J. Inst. Elect. Eng. 93, 1946, pp. 429-441; and Sheng et al., "Experiments on Pattern Recognition Using Invariant Fourier-Mellin Descriptors," Journal of Optical Society of America, vol. 3, No. 6, June, 1986, pp. 771-776, the disclosures of which are incorporated herein by reference.

Figure 15:
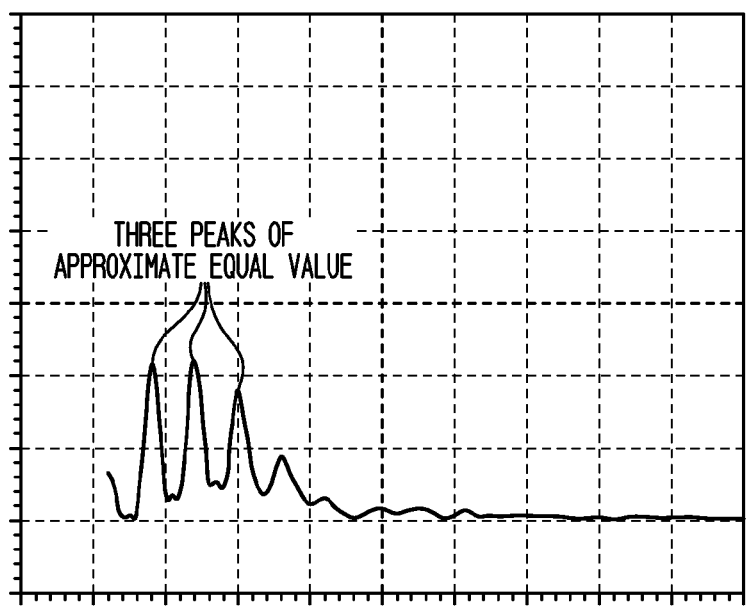
FIG. 15 shows frequency spectra of Analog Devices ADX L. 204 accelerometer with no load.

As shown in FIG. 14, an ADX L 204 accelerometer 110 is positioned on one of the inflation bladders 112 of a Stryker Model 2950 bed 113. A Tektronix Model TDS 3034 digital recording oscilloscope 108 with TTS 3 FFT, FFT Applications Module (part 017-0305-01) is used to gather the preliminary data. FIG. 15 shown the data gathered with no load on the surface of the inflation bladder 112.

Figure 16:
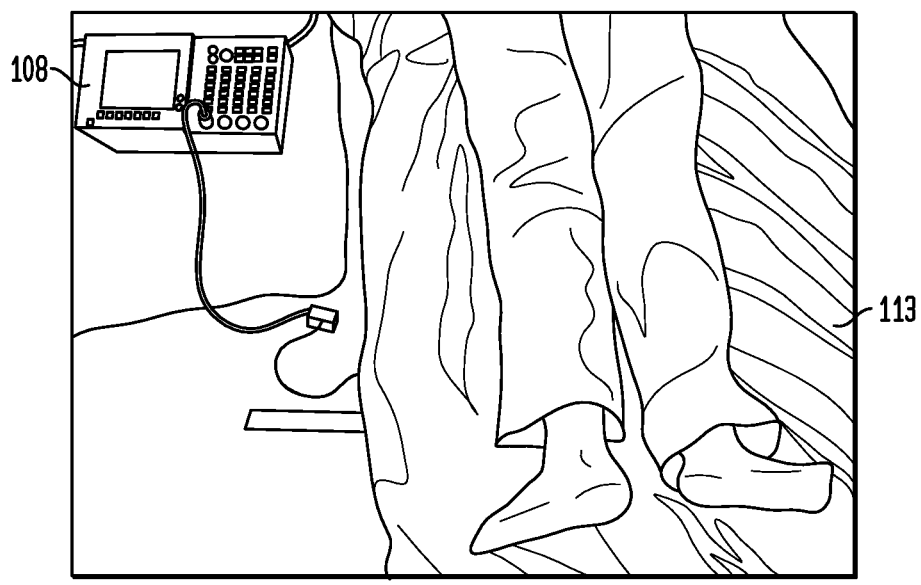
FIG. 16 shows human bony tissue situated over measurement means.
Figure 17:
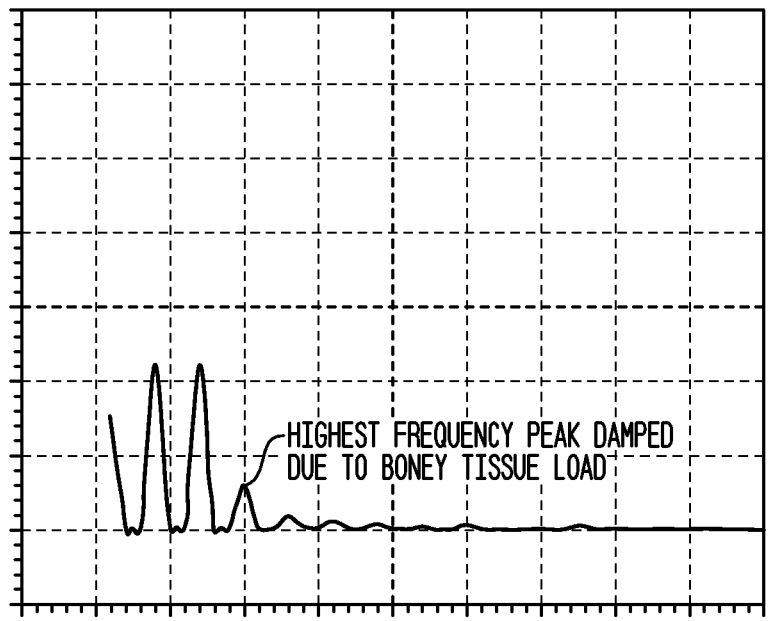
FIG. 17 shows frequency spectra from bony tissue situated over an accelerometer.

FIG. 16 shows a bony portion of one's leg placed over the accelerometer 110. The frequency spectra data gathered is shown in FIG. 17. On examining this data, it is shown that the right side of the data has a substantial decrease in amplitude in comparison to the no load situation in FIG. 15. Thus it is apparent which test examples are unloaded, and which are loaded with bony tissue.

Figure 18:
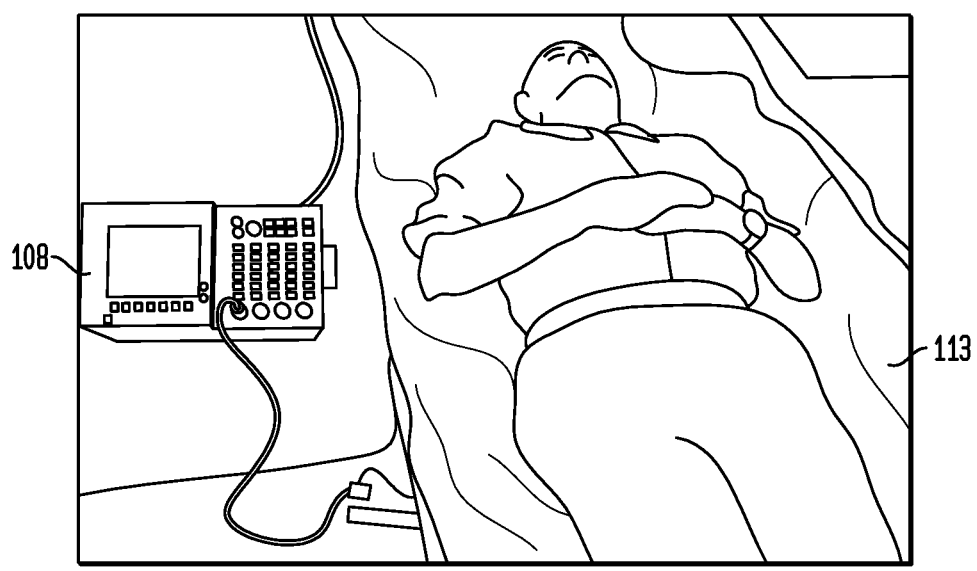
FIG. 18 shows human adipose tissue situated over measurement means.
Figure 19:
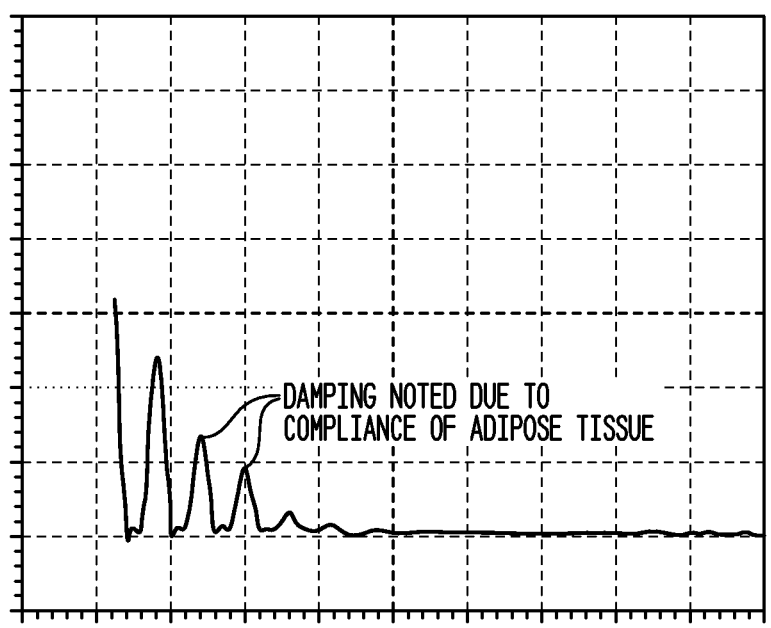
FIG. 19 shows frequency spectra from adipose tissue.

The test subject's adipose tissue is next situated over the accelerometer 110. The test configuration is shown in FIG. 18. Through an examination of the data shown in FIG. 19, the adipose tissue significantly dampens the higher frequency spectra. Accordingly, the present invention makes it possible to differentiate adipose tissue from leg tissue and also from a situation where there is no loading on the accelerometer 110.

Example 4

Figure 20:
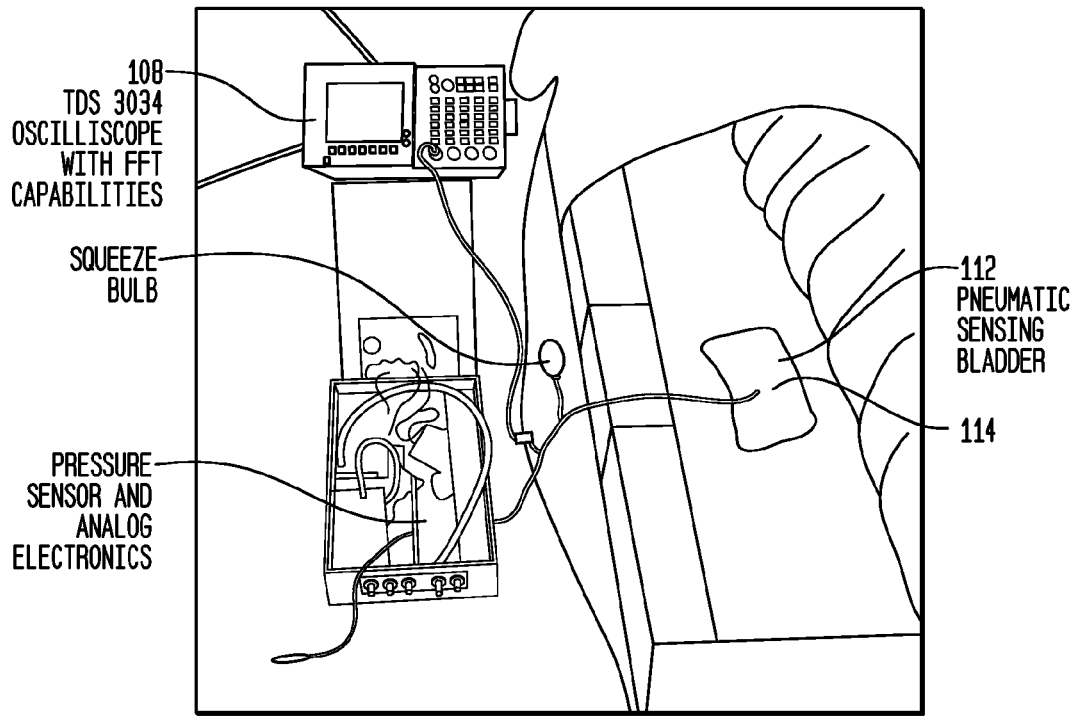
FIG. 20 shows an apparatus for FFT tissue characterization measurement from pneumatic pressure sensor.
Figure 21:
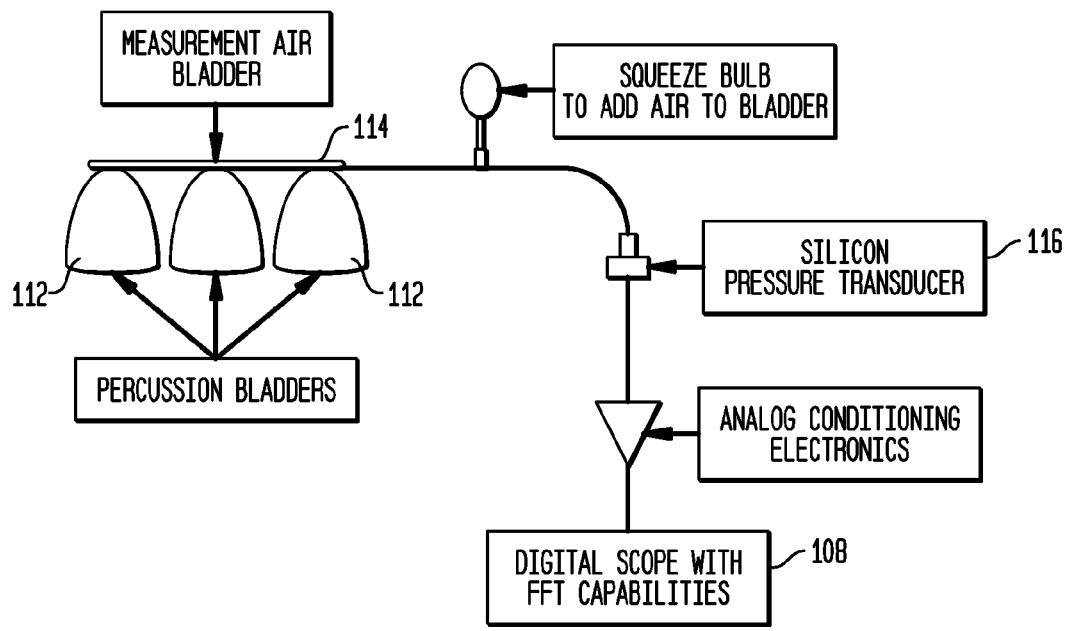
FIG. 21 is a block diagram of an apparatus for FFT tissue characterization.

In addition to performing FFT tissue characterization analysis with accelerometer sensors, one can also determine tissue types from data generated by a pneumatic pressure sensor, then analyzed using the FFT method. For this example the kinetic energy can be supplied by a small inflation bladder 112 in continuous inflation/deflation oscillation and a measurement bladder 114 in conjunction with a pressure transducer 116 used to measure the absorption of this energy by the tissue placed over the measurement bladder, as shown in FIG. 20. A block diagram of the apparatus is shown in FIG. 21.

Figure 22:
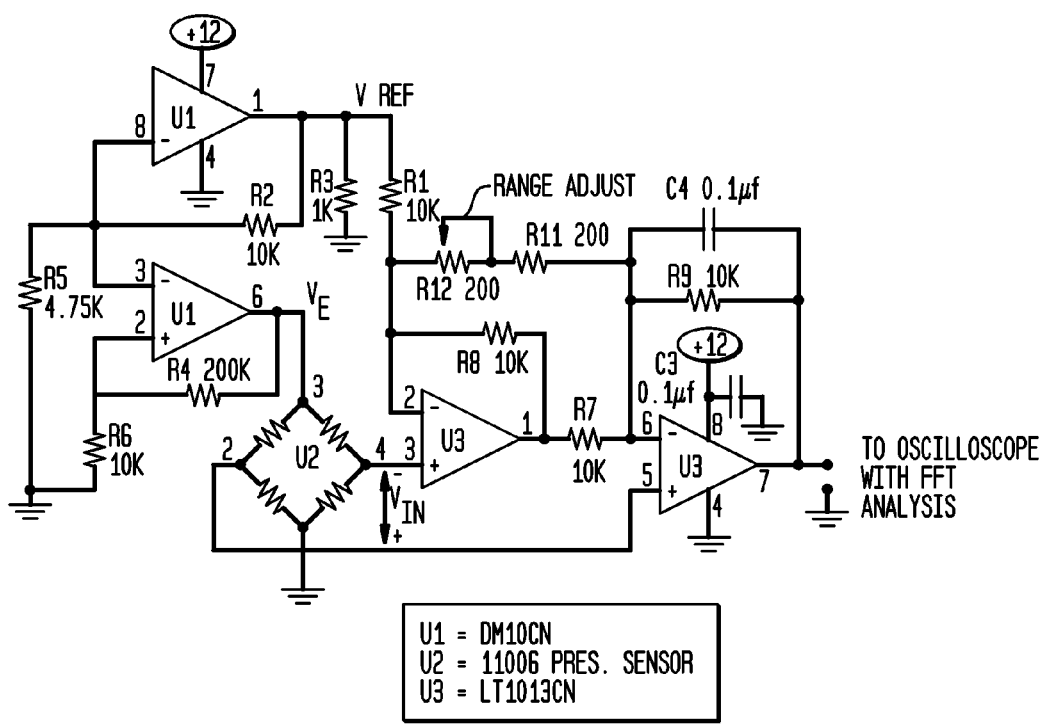
FIG. 22 is an analog conditioning circuit for pressure transducers used in pneumatic FFT experiments.
Figure 23:
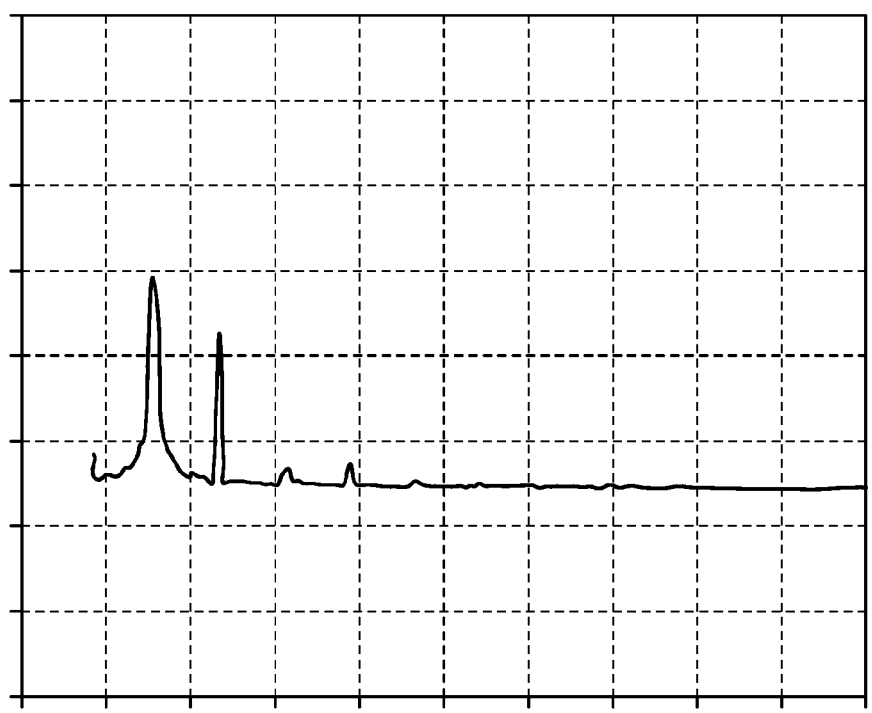
FIG. 23 shows an unloaded bladder FFT data measured by means of a pneumatic sensor.

A squeeze-bulb is provided to partially fill the measurement bladder 114 with air and it is connected to a type Lucas 11006 silicon pressure transducer 116. The transducer is configured in a Wheatstone bridge. In addition to the Wheatstone bridge there is additional analog conditioning electronics, as shown in the schematic in FIG. 22. The pressure signal is fed to a Tektronics Model TDS 3034 digital oscilloscope 108, which has FFT analysis capabilities. The schematic of the analog conditioning electronics is shown in FIG. 22. Unloaded bladder FFT data measured by means of the pneumatic sensor is shown in FIG. 23.

Figure 24:
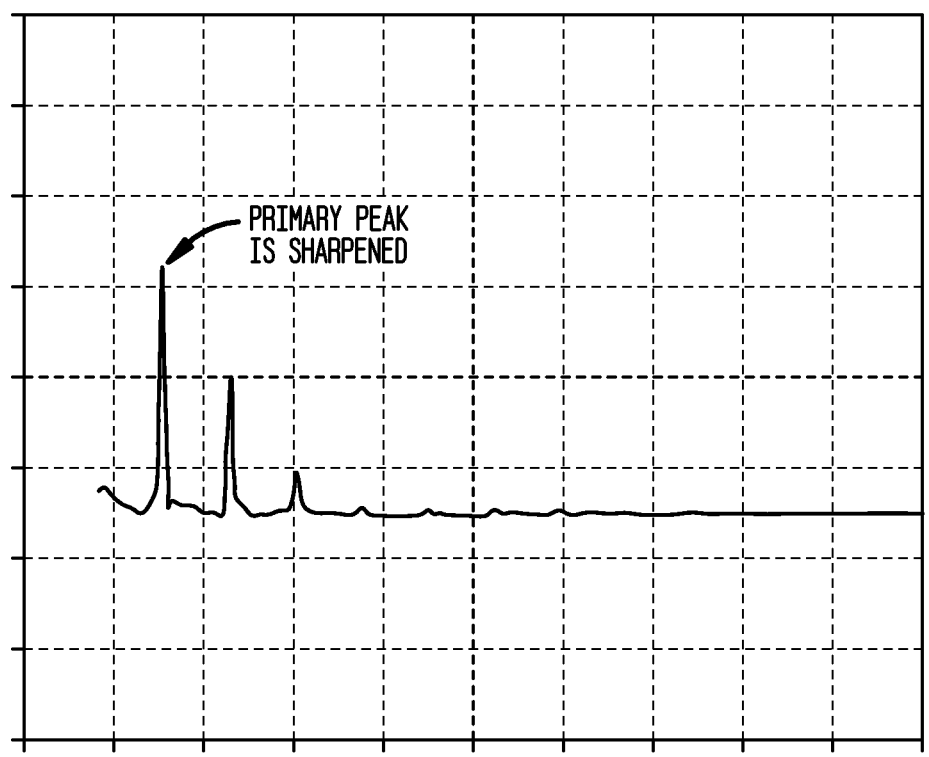
FIG. 24 shows a bony tissue spectrogram from pneumatic FFT sensor analysis.
Figure 25:
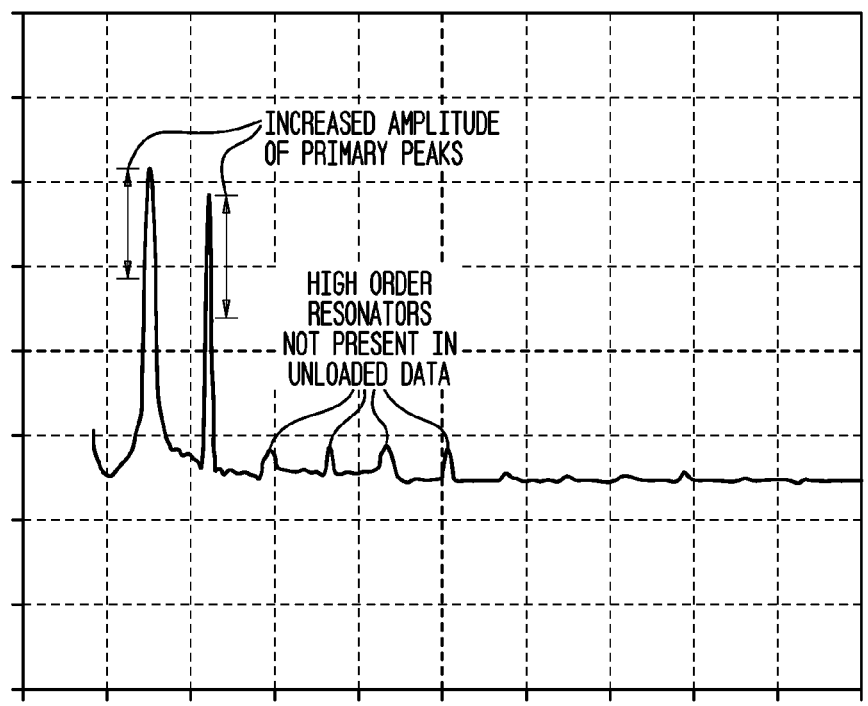
FIG. 25 shows an adipose tissue spectrogram taken by placing the inventor's buttocks over the sensing area.

A second measurement of bony tissue, performed in an identical manner to the data previously acquired by means of an accelerometer and FFT analysis, is shown in FIG. 24. This data shows that the width of the mean peak has been significantly narrowed and that the higher frequency components have gained amplitude compared to the unloaded signal. Now turning to the adipose tissue data as shown in FIG. 25, it can be seen that the primary peaks have increased in amplitude, and high order resonators, not present before, can now be seen.

As thus far described, this data, like the previous accelerometer data, enables the computer system controlling the surface to sort out the various tissue types based upon the FFT analysis. Through this algorithm it is possible to provide optimized care for the patient on a segment-by-segment basis.

Example 5—Bladder Inflation Signal Generating Means

Figure 26:
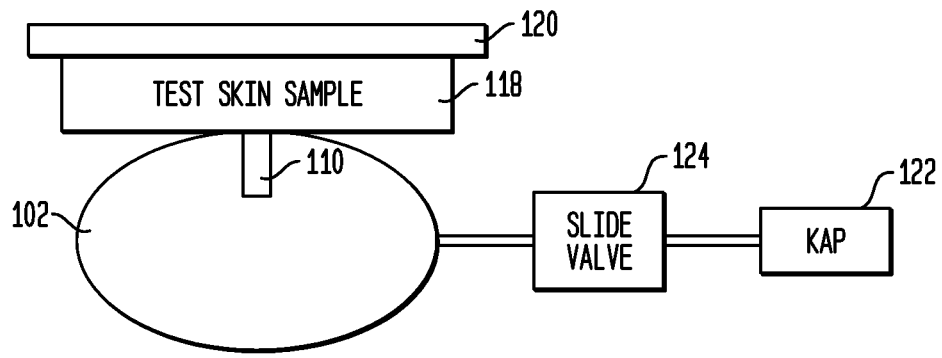
FIG. 26 is a cross sectional schematic of an air cushion.

In accordance with another embodiment as shown in FIG. 26, kinetic energy is supplied by inflating a floatation bladder 102 as a step function with the sensor being an accelerometer 110 mounted inside the bladder. Artificial tissue phantoms 118 were used to collect the data. As described below, the result on this example is shown in two parts. In the first part each artificial tissue phantom 118 is placed individually on the apparatus and data is gathered. In the second part the two extremes of tissue, skin over sacrum/scapula and skin over adipose deposit, are placed side-by-side on a sensor array and simultaneous data is taken.

Six artificial tissue phantoms 118 where obtained from EC Services of Centerville Utah. These polymers which represent skin ranged from very hard to extremely soft and were affixed to pieces of birch plywood 120 which represents bone. These samples were mounted on top of the apparatus, which consisted of the floatation bladder 102 which contained the accelerometer sensors 110. A schematic diagram of a cross section of this configuration is shown in FIG. 26.

The floatation bladder 102 is connected in parallel to one of the cell-pairs in a Model K-4oem, pressure relief surface manufactured by KAP medical of Corona, Calif. This surface is operated in the "therapy" mode in which air is continuously supplied to all the cells, and the fan is set to level 8. Between the floatation bladder 102 which contains the accelerometer 110 and the KAP 122 pressure relief surface serving as the air source, a slide-valve 124 is placed. This valve enables the floatation bladder to be filled and exhausted such that the accelerometers contact the tissue sample upon tube full expansion and "snapshots" of data can be collected with the oscilloscope 108. These snapshots of data are recorded by the oscilloscope, analyzed with the FFT software and subsequently stored in a spreadsheet format for further analysis.

Spectral Measurements Methods

Frequency Space Measurement

The adaptation of frequency space measurements to the apparatus shown in FIG. 26 is as previously described with respect to Example 3.

Power Spectra Measurement

In accordance with another embodiment, a power spectra analysis means can be used. The measurement means is based on the fact that the decay of stored kinetic energy in the accelerometer 110 after impact is dependent on the amount of damping provided by the tissue. Therefore through integration of the waveform it is possible to directly measure this stored kinetic energy (power spectra). This is shown in the FIG. 27.

Figure 27:
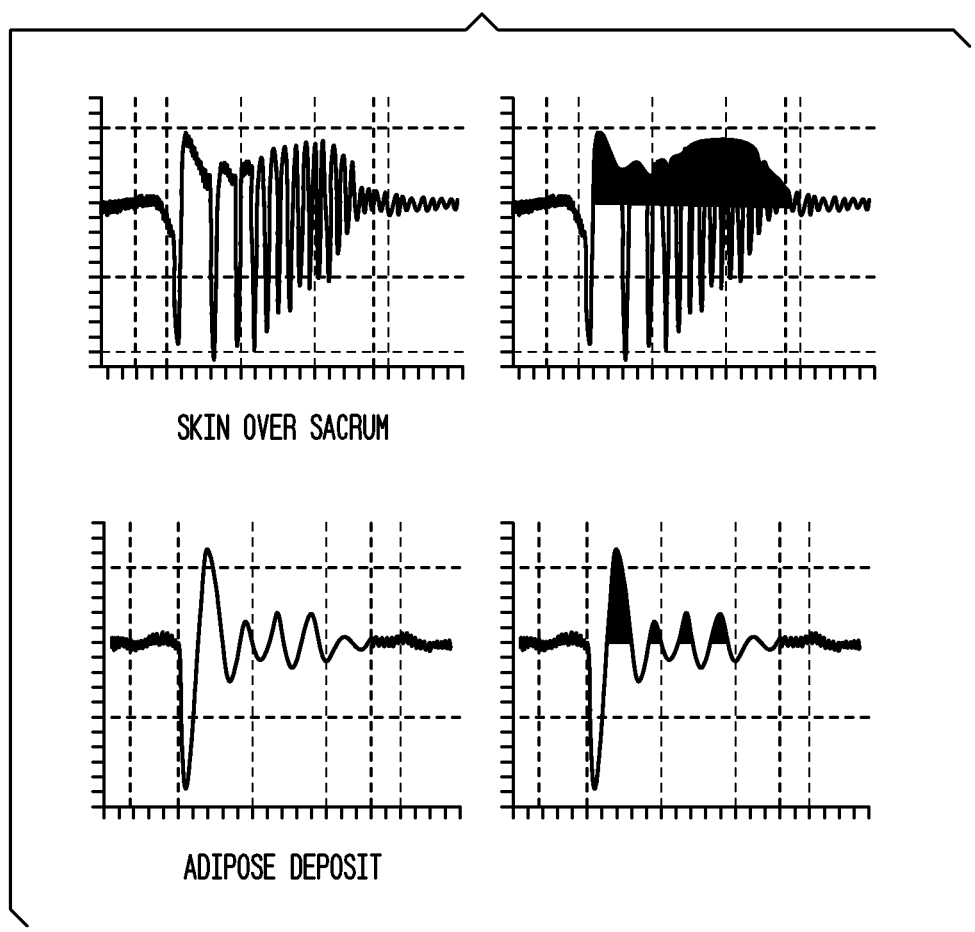
FIG. 27 shows data using power spectra analysis.

This measurement method can be understood by examining the waveforms from the frequency space data. For example, when the accelerometer 110 is in contact with the hard tissue, it takes a longer time for the kinetic energy to be dissipated into heat. This is shown in FIG. 27. For very flaccid tissue this takes fewer cycles of oscillation. This is also shown in FIG. 27.

Figure 28:
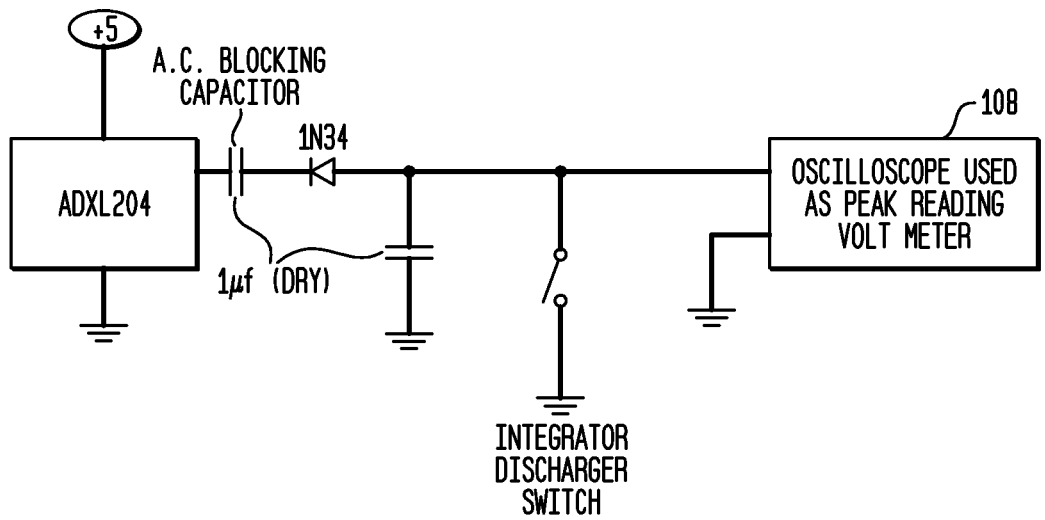
FIG. 28 is a power spectra integrator which provides a means to analyze the sensor data.

For the purposes of this embodiment, the circuit was accomplished through the use of a half wave rectifier and integrating capacitor. A germanium diode was selected for the half wave rectifier because of its low, 230 mV band gap. This band gap was sufficiently low to pass the accelerometer signal yet high enough to block noise from being integrated by the capacitor. A switch was provided to discharge the capacitor between the examples and the oscilloscope 108 employed as a peak reading volt meter. A schematic diagram of this circuit is shown in FIG. 28.

Skin Classification Data with Frequency Space Measurements

Figure 29:
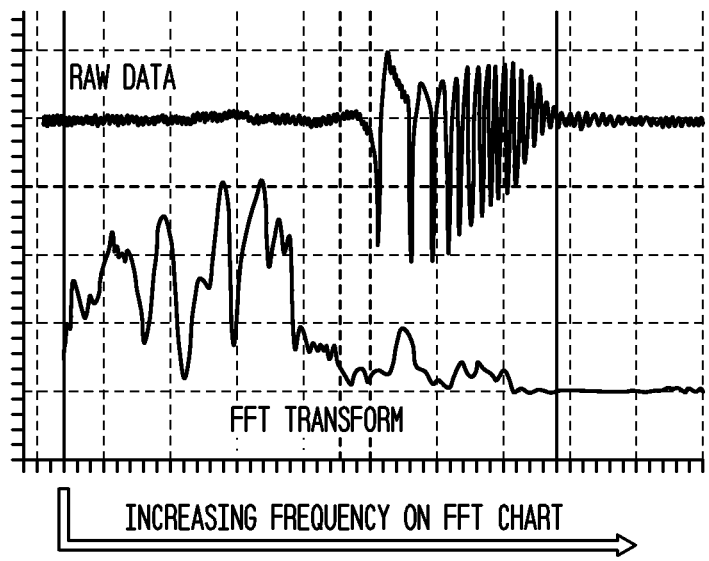
FIG. 29 is a frequency graph of skin over sacrum/scapula.
Figure 30:
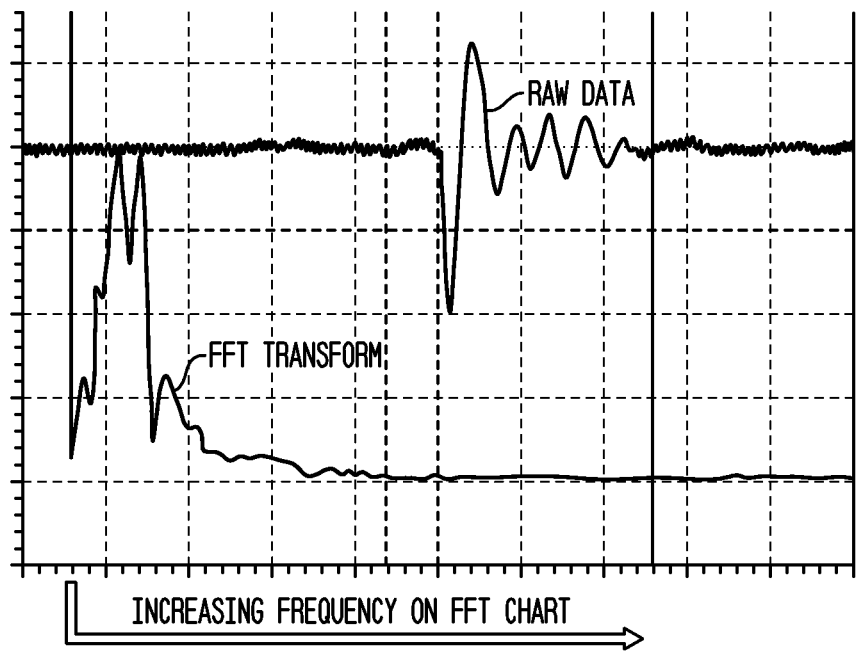
FIG. 30 is a frequency graph of skin over adipose deposit, pannus of obese individual.
Figure 31:
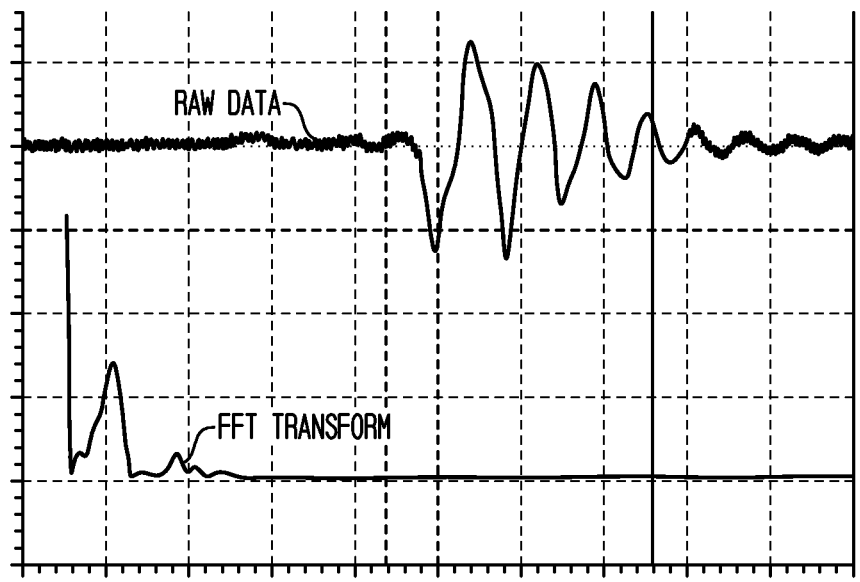
FIG. 31 is a frequency graph of a sensor with no load.

The data from skin classification using frequency space measurements is shown in the FIGS. 29-31. FIG. 29 is the "hardest" tissue sample representing skin over bone, sacrum/scapula. The data continues with decreasing levels of hardness with the data from the most flaccid tissue shown in FIG. 30, adipose deposit, pannus of obese individual. FIG. 31 is the data from the accelerometer 110 with no load. For each sample, the raw data from the accelerometer is shown in the upper portion of the figure and the FFT frequency space transform is shown in the lower portion of the figure.

It is therefore possible according to this embodiment of the invention to identify and classify the various tissue types.

Skin Classification Data with Power Spectra

Thirty-two replicate measurements are made with each tissue phantom 118 and the average results are shown below in millivolts of peak signal measured across the integrating capacitor.

| Tissue sample | Mean reading in millivolts | standard deviation |
|---|---|---|
| Skin over sacrum/scapula | 779.6 | 8.5 |
| Skin over Achilles tendon insertion | 712.3 | 12.2 |
| Skin over toned muscle mass | 646 | 11.4 |
| Skin over trocanter | 499.7 | 7.1 |
| Skin over flaccid biceps | 463.3 | 17.4 |
| Skin over adipose deposit | 446.1 | 8.4 |

It is therefore possible according to this embodiment of the invention to identify and classify the various tissue types.

Dual Sensor Array

Figure 32:
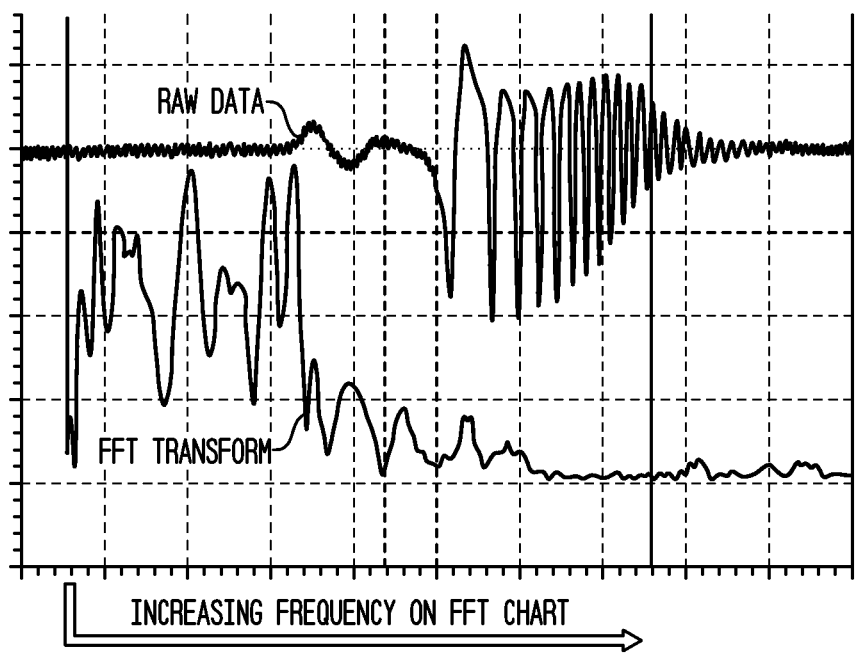
FIG. 32 is a frequency graph of skin over sacrum/scapula measured with two sensor array.
Figure 33:
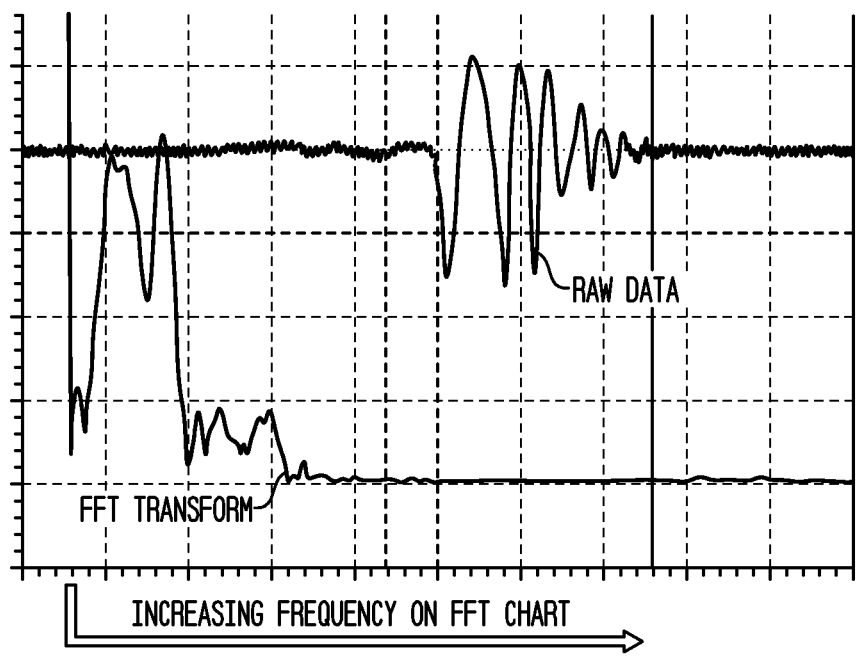
FIG. 33 is a frequency graph of skin over adipose deposit measured with two sensor array.

The hardest and most flaccid tissue samples were place side-by-side on a two accelerometer array in which these sensors were spaced by 3 cm. Data is taken with the first accelerometer of the skin over sacrum/scapula sample and then the skin over adipose deposit utilizing the second accelerometer. The data is shown in FIGS. 32 (sacrum/scapula) and 33 (adipose deposit). It is therefore possible according to this embodiment of the invention to identify and classify the various tissue types.

Example 6

The preferred embodiment of the invention is to provide the kinetic energy excitation signal as an impulse function by mechanically moving the accelerometer sensor 110, positioned internally or externally on the bladder, a short distance away from a particular area of the patient's tissue and then allowing the accelerometer to rapidly accelerate and make contact with this tissue. This embodiment enables more exact control over the kinetic energy imparted into a particular area of a patient's tissue.

This embodiment also is preferred because the mechanical movement of the accelerometer is such that it can impart a pulse of mechanical energy into the tissue at a low cost implementation. This embodiment takes advantage of the spring action of the floatation bladder 102 to rapidly accelerate the accelerometer sensor into the tissue at a predefined location. There are a variety of mechanical embodiments which can obtain this type of mechanical excitation, one example shown in FIG. 34.

Figure 34:
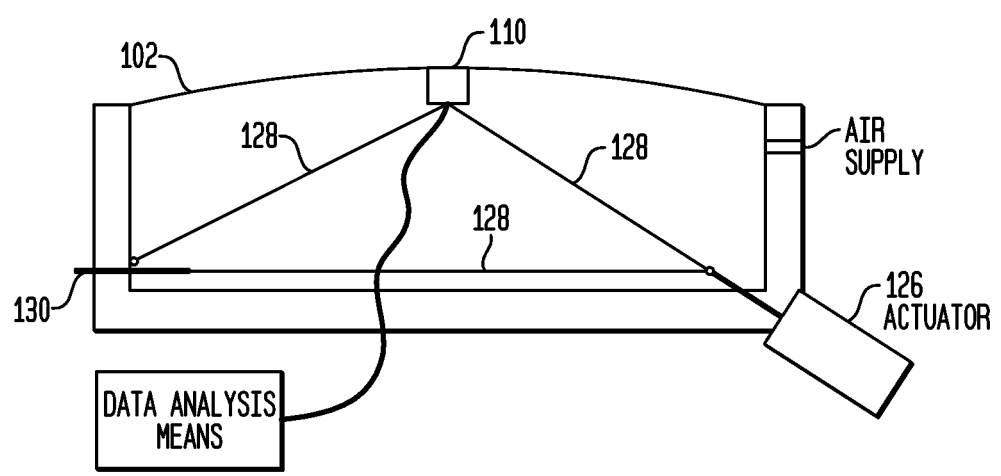
FIG. 34 is an illustration of a mechanical means used to impart a pulse of kinetic energy into tissue shown in the relaxed position.

The floatation bladder 102 shown in FIG. 34 is substituted for one of the air bladders is a model K-4oem, pressure relief surface manufactured by KAP medical of Corona, Calif. The preferred accelerometer 110 is the Analog Devices model AXL204. For this configuration the output of the accelerometer sensors is recorded with a Tektronics model TDS3034 digital recording oscilloscope 108. This oscilloscope has the TDS3FFT, FFT applications module, which is used for the frequency space analysis.

Figure 35:
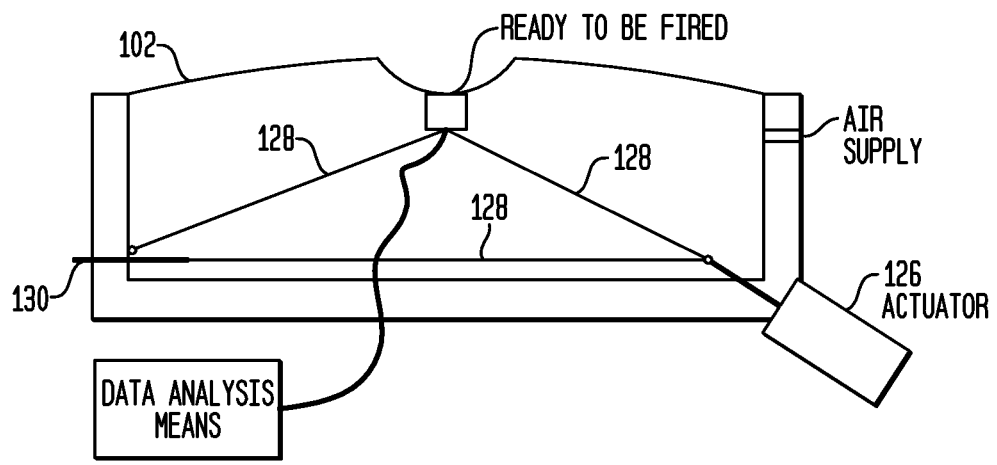
FIG. 35 is an illustration of a mechanical means used to impart a pulse of kinetic energy into tissue shown in the ready position.
Figure 36:
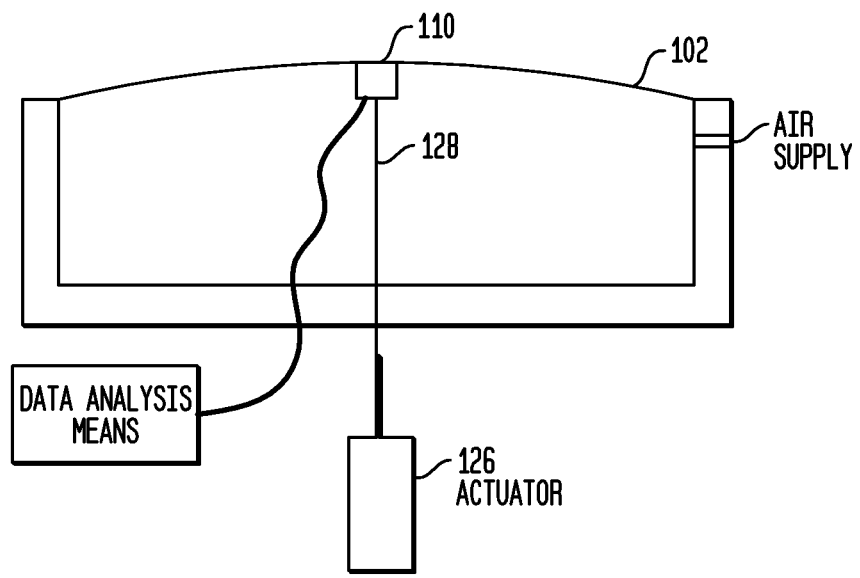
FIG. 36 is an illustration of a mechanical means used to impart a pulse of kinetic energy into tissue shown in the relaxed position in accordance with another embodiment of the invention.
Figure 37:
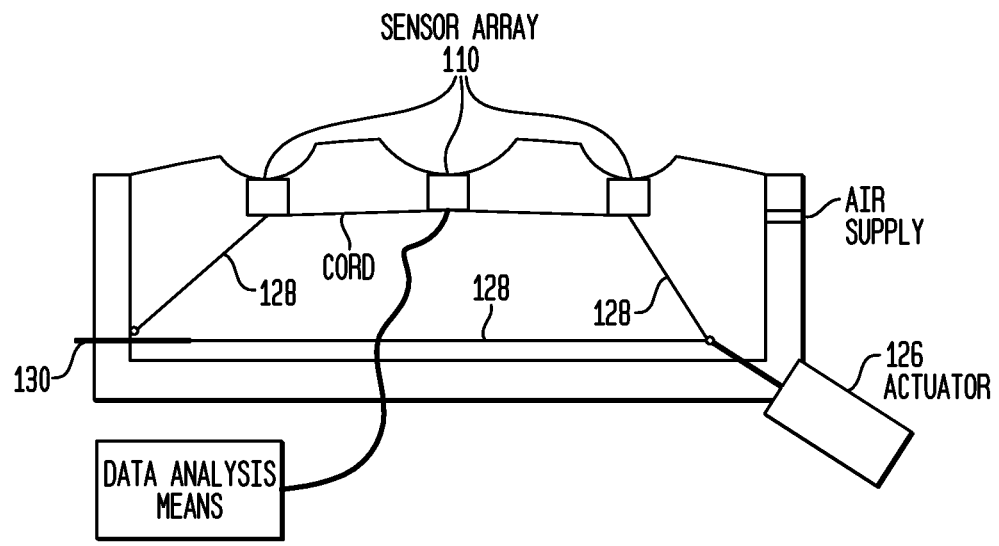
FIG. 37 shows an array of sensors impart kinetic energy into the patient with a common actuator.

As shown in FIGS. 34 and 35, an actuator 126 such as an air cylinder is attached to one end of a cord 128. The cord 128 is attached to the accelerometer 110 and its other end to the sidewall of the floatation bladder. The actuator pulls on the chord to move the accelerometer 110 into the "ready" position when it is pulled into the floatation bladder 102 a short distance. The actuator 126 then abruptly relaxes the cord 128 and the accelerometer, due to the resiliency of the inflated floatation bladder, snaps back into the relaxed position imparting a single pulse of kinetic energy into the patient, which is subsequently, analyzed with the data analysis means. An optional tensioner 130 may be used to maintain the cord under zero tension at rest. In another embodiment shown in FIG. 36, the actuator 126 is located directly beneath the accelerometer 110. In still another embodiment of the invention, energy pulses are imparted into an array of accelerometers 110 running along the length of the floatation bladder as shown in FIG. 37.

Figure 38:
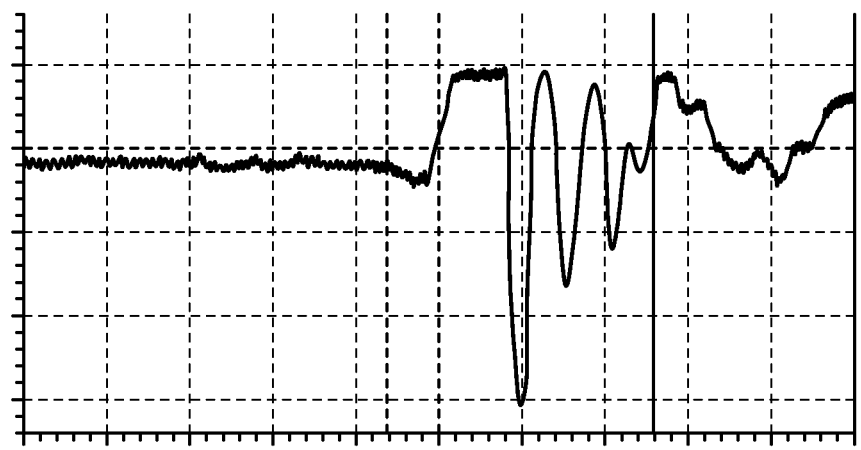
FIG. 38 shows frequency data from adipose tissue phantom.
Figure 39:
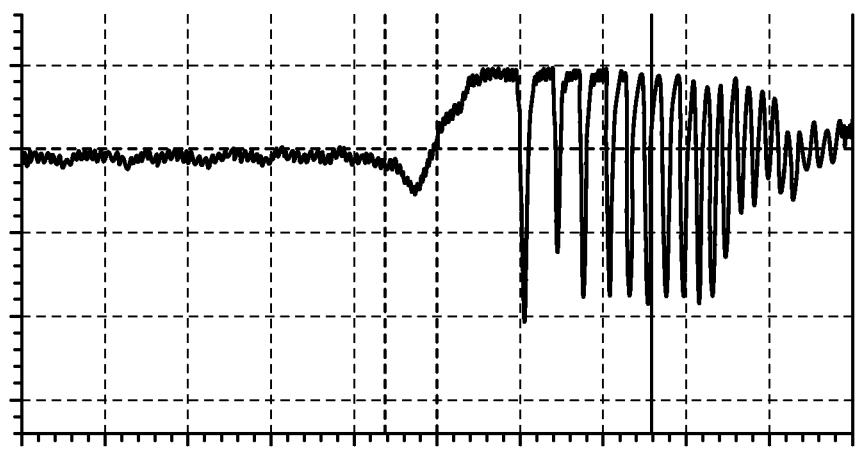
FIG. 39 shows frequency data from skin-sacrum tissue phantom.

Data from the preferred embodiment is shown in FIGS. 38 (adipose tissue) and 39 (sacrum tissue). The data from FIGS. 38 and 39 show that the kinetic energy impulse function that is imparted by the accelerometer sensor is rapidly dissipated by the adipose tissue and it is poorly dissipated by the sacrum tissue.

Example 7

Figure 40:
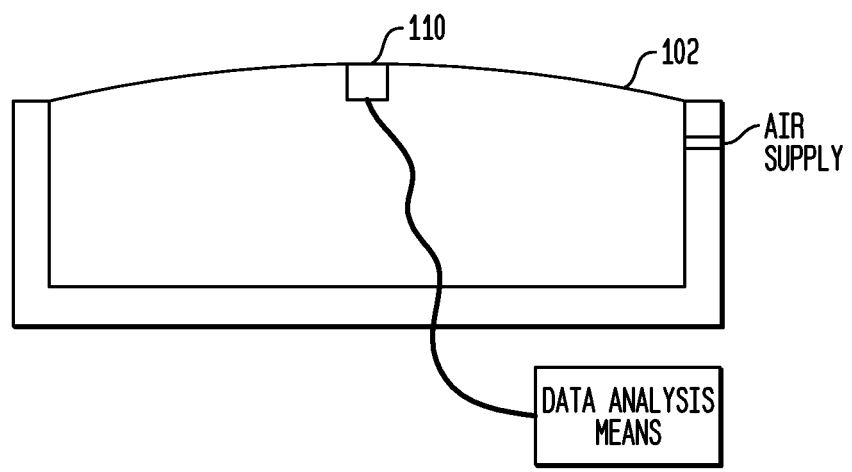
FIG. 40 illustrates kinetic energy from patient movement utilized to provide tissue characterization signal.
Figure 41:
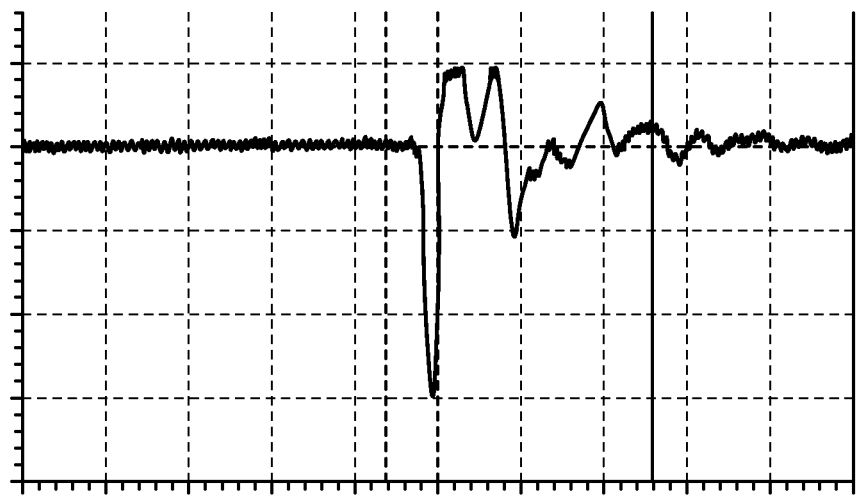
FIG. 41 shows highly damped signal detected from placing adipose deposit skin phantom over detector.
Figure 42:
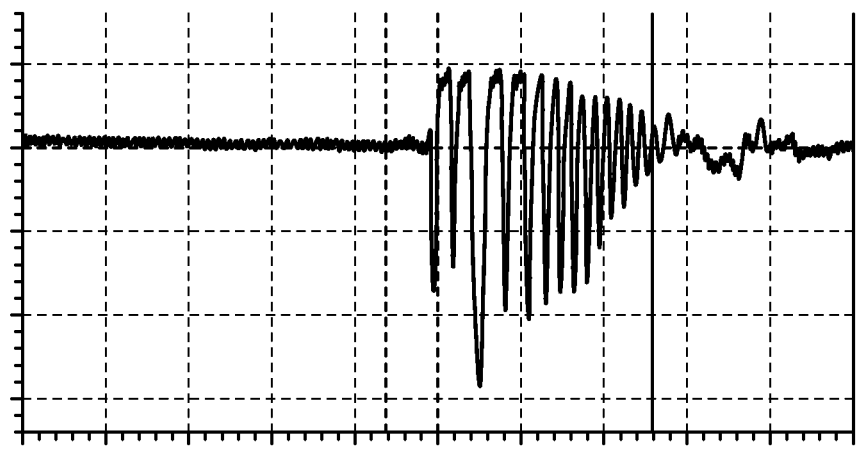
FIG. 42 is a frequency graph of skin over sacrum phantom placed over the sensor.

In the previous examples the source of the kinetic energy has been an external pneumatic power source to provide the kinetic energy for the measurement means. It is also contemplated to obtain data in which the movement of the patient on the surface provides the required kinetic energy excitation impulse. This kinetic energy inducing movement can be provided by the patient or could be provided by an external agent such as the care provider turning the patient on the surface. In either case, when a particular area of a patient is forced into contact with an accelerometer sensor 110 attached to the surface of a floatation bladder 102 as shown in FIG. 40 useful data can be acquired. FIG. 41 shows a highly damped signal detected from placing adipose deposit tissue phantoms over an accelerometer 110. Alternatively shown in FIG. 42, when the tissue sacrum phantom is placed over the accelerometer, a poorly damped signal is detected.

These two pieces of information when combined will provide a composite picture of where the patient is located on a particular surface and the types of tissue along with their geographical arrangement of the tissues on that surface.

The principles of the present invention are also adaptable to detect/characterize various tissues through conventional bed clothing. For example, the invention is adaptable for use with patients wearing pajama material. It has been discovered that cotton cloth has little impact on the signal fidelity. When this material is subsequently wetted with water, simulating a leaking wound, the data shows a reduction in the length of the raw data signal evidencing the presence of water. In another example, Depend™ protective underwear fabric causes attenuation of the accelerometer signal but does not appreciably alter the waveform characteristics. When this material is subsequently wetted with water, simulating soiled underwear, it can be seen that the signal returns back to an amplitude, which is comparable to the signal with no fabric covering. The effect of wetting results in a noticeable signal change.

In accordance with the present invention, the use of various sensors and frequency space or rate based analysis, and specifically by means of frequency space analysis, it is possible not only to determine where the patient is located on the surface but also their distribution of tissue type. This would enable the surface to determine if the patient is sitting or lying on the surface, where they are located on the surface, and then by recording this information over time, their level of mobility.

Given the level of data that is available through frequency space or rate based analysis, it is contemplated that the entire surface could be controlled on the basis of the information gathered. Even more information may be gained through the combination of this information with other information such as thermograph. Pattern analysis means, which utilize multi-dimensional dimension matrices of data, are commonly known. Through this characterization, it is possible to predict the location of a bedsore on a particular location on a patient's prior to its physical appearance. The novel method of controlling a pressure relief surface has significant advantages over the narrow bandwidth, amplitude sensing systems currently employed. These advantages include the ability to precisely control the surface based on the patient's configuration of tissue such that each patient is receiving optimal care wherever they are located on the surface.

Linking a hospital bed to a network communication system is well known. Examples include U.S. Pat. Nos. 7,315,535, 5,561,412, 5,699,038 and 5,838,223 which are incorporated herein by reference. In the past such networks have been used for bed monitoring such as mattress firmness and patient incontinence. In addition, U.S. Pat. No. 6,279,183 teaches more advanced information passing through the network such as bed articulation angles, brakes, bed exit, as well as other variables. With the sensors of the present invention, it is possible to pass diagnostic information on the patient's bedsore development and status, incorporating this information along with patient mobility on the treatment surface through a network to the hospital information system. Therefore, the hospital information system can now monitor and chart changes in the patient's tissue status continuously during the patients stay for legal, insurance and clinical care plan protocols. The caregiver can now routinely check patient bedsore status at a remote nurse master station rather than having to make manual measurements during bed check rounds. A history of the tissue status for a particular patient can be displayed on a graphical user interface, which may incorporate a patient avatar such as that disclosed in U.S. Pat. No. 7,555,436 as a means to disclose tissue status, the disclosure of which is incorporated herein by reference. In addition it will be possible to download this data to a data file and/or route via the network to a remote location.

It can be seen that the illustrated embodiments employs pneumatic means to supply the kinetic energy which performs the work on the tissue of interest and subsequent data is derived with either an accelerometer or pressure transducer, it is within the inventive concepts herein disclosed to employ other methods to supply this kinetic energy and other methods to detect the data. For example, the kinetic energy could be supplied by a moveable strap rather than an air bladder and the detection means could be a strain gauge type sensor placed in series with this strap in place of the accelerometer or pressure transducer. This invention can also be used in wheel chair cushions or other surfaces used by persons in risk of developing bedsores and other skin related ulcers. This invention can also be used in operating room tables, examination chairs and dental chairs to reduce the risk of developing bedsores and other skin related ulcers.

This invention can also be used in automotive, marine and aviation applications where persons must sit for protracted periods of time. Here the invention concepts could be used to provide seating that automatically adjusts for a particular person's anatomy and seating or lying on a surface during a particular time in a journey.

The invention can also be used in mass-market consumer mattresses or cushions by persons suffer from muscle and connective tissue pain due to debilitating fatigue, sleep disturbance, and joint stiffness. Examples include individuals suffering from fibromyalgia, chronic fatigue syndrome, multiple sclerosis and the like.

Since certain changes may be made in the above products without departing from the scope of the invention herein involved, it is intended that all matter contained in the above description, or shown in the accompanying drawings, shall be interpreted as illustrative and not in a limiting sense.

Thus the scope of the invention should be determined by the appended claims and their legal equivalents, rather than by the examples given.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for characterizing human tissue type comprising:
   a surface adapted for applying a single pulse of kinetic energy to an anatomical portion of a human supported on the surface;
   at least one sensor associated with said surface, the at least one sensor collecting data reflective of a rate of dissipation of the applied single pulse of kinetic energy, whereby the rate of dissipation of the applied single pulse of kinetic energy is indicative of the tissue type of said anatomical portion; and
   a processor programmed for (1) processing the data collected by said at least one sensor relating to said rate of dissipation of the applied single pulse of kinetic energy and (2) using the processed data based on the rate of dissipation of the applied single pulse of kinetic energy to characterize the tissue type of said anatomical portion.

2. The apparatus of claim 1, wherein said surface comprises a portion of at least one first inflatable bladder.

3. The apparatus of claim 2, further including a second inflatable bladder having a volume supporting said first inflatable bladder, wherein said first inflatable bladder has a volume greater than the volume of said second inflatable bladder.

4. The apparatus of claim 1, wherein the processor is further programmed for processing the data collected to identify a location of the anatomical portion of the human.

5. The apparatus of claim 1, wherein characterizing the tissue type comprises the processor programmed to compare the processed data to predetermined data representative of different tissue types.

6. The apparatus of claim 1, wherein processing the data collected comprises the processor programmed to analyze the collected data in frequency domain.

7. The apparatus of claim 1, wherein the at least one sensor comprises an accelerometer.

8. An apparatus for characterizing human tissue type comprising:
   a surface adapted for applying a single pulse of kinetic energy to an anatomical portion of a human supported on the surface;
   at least one accelerometer associated with said surface, the at least one accelerometer collecting data reflective of a rate of dissipation of the applied single pulse of kinetic energy, whereby the rate of dissipation of the applied single pulse of kinetic energy is indicative of the tissue type of said anatomical portion; and
   a processor programmed for (1) processing the data collected by said at least one sensor relating to said rate of dissipation of the applied single pulse of kinetic energy, (2) using the processed data based on the rate of dissipation of the applied single pulse of kinetic energy to characterize the tissue type of said anatomical portion, and (3) comparing the processed data to predetermined data representative of different tissue types.

9. The apparatus of claim 8, wherein the processor is further programmed for processing the data collected to identify a location of the anatomical portion of the human.

10. The apparatus of claim 9, further including a second inflatable bladder having a volume supporting said first inflatable bladder, wherein said first inflatable bladder has a volume greater than the volume of said second inflatable bladder.

11. The apparatus of claim 10, wherein processing the data collected comprises the processor programmed to analyze the collected data in frequency domain.

12. The apparatus of claim 11, wherein processing the data collected comprises the processor programmed to analyze the collected data in frequency domain.

* * * * *